United States Patent [19]

Bisgård-Frantzen et al.

[11] Patent Number: 6,093,562

[45] Date of Patent: *Jul. 25, 2000

[54] AMYLASE VARIANTS

[75] Inventors: Henrik Bisgård-Frantzen, Lyngby; Allan Svendsen, Birkeroed; Torben Vedel Borchert, Copenhagen N, all of Denmark

[73] Assignee: Novo Nordisk A/S, Bagsvaerd, Denmark

[*] Notice: This patent issued on a continued prosecution application filed under 37 CFR 1.53(d), and is subject to the twenty year patent term provisions of 35 U.S.C. 154(a)(2).

[21] Appl. No.: 08/600,656

[22] Filed: Feb. 13, 1996

Related U.S. Application Data

[63] Continuation of application No. PCT/DK96/00056, Feb. 5, 1996.

[51] Int. Cl.⁷ .................................................. C12N 9/28
[52] U.S. Cl. .......................... 435/202; 510/226; 510/236; 510/530; 510/320; 510/392
[58] Field of Search .................. 435/202, 172.3; 510/226, 236, 530, 320, 392

[56] References Cited

U.S. PATENT DOCUMENTS 4,600,693  7/1986  Kindle et al. ........................... 435/176

FOREIGN PATENT DOCUMENTS

| | | |
|---|---|---|
| 2 665 178 | 1/1992 | France . |
| 2 676 456 | 11/1992 | France . |
| 87/00202 | 1/1987 | WIPO . |
| 91/00353 | 1/1991 | WIPO . |
| 91/16423 | 10/1991 | WIPO . |
| 94/02597 | 2/1994 | WIPO . |
| 94/18314 | 8/1994 | WIPO . |
| 95/10603 | 4/1995 | WIPO . |
| 95/21247 | 8/1995 | WIPO . |
| 95/26397 | 10/1995 | WIPO . |
| 95/35382 | 12/1995 | WIPO . |

OTHER PUBLICATIONS

Tsukamoto, A., et al., Biochem. and Biophys. Res. Com., vol. 151, No. 1, pp. 25–31 (1988).
Estell, D.A., et al., The Jour. Biol. Chem., vol. 260, No. 11, pp. 6518–6521 (1985).
Abstract—Dialog, File 351, Derwent WPI, Dialog Accession No. 007176688 (1987).
Suzuki, Y., et al., The Jour. of Biol. Chem., vol. 264, No. 32, pp. 18933–18938 (1989).
Chemical Abstracts, vol. 112, No. 15, The Abstract No. 135178r, p. 347 (1990).
Chemical Abstracts, vol. 108, No. 11, The Abstract No. 90927h, p. 325 (1988).
Chemical Abstracts, vol. 112, No. 19, The Abstract No. 174785f, p. 350 (1990).

*Primary Examiner*—Rebecca E. Prouty
*Attorney, Agent, or Firm*—Steve T. Zelson, Esq.; Reza Green, Esq.

[57] ABSTRACT

The present invention relates to variants of a parent α-amylase, which parent α-amylase (i) has an amino acid sequence selected from the amino acid sequences shown in SEQ ID No. 1, SEQ ID No. 2, SEQ ID No. 3, and SEQ ID No. 7, respectively; or (ii) displays at least 80% homology with one or more of these amino acid sequences; and/or displays immunological cross-reactivity with an antibody raised against an α-amylase having one of these amino acid sequences; and/or is encoded by a DNA sequence which hybridizes with the same probe as a DNA sequence encoding an α-amylase having one of these amino acid sequences; in which variant:

(a) at least one amino acid residue of the parent α-amylase has been deleted; and/or (b) at least one amino acid residue of the parent α-amylase has been replaced by a different amino acid residue; and/or (c) at least one amino acid residue has been inserted relative to the parent α-amylase; the variant having α-amylase activity and exhibiting at least one of the following properties relative to the parent α-amylase: increased thermostability; increased stability towards oxidation; and reduced $Ca^{2+}$ dependency;

with the proviso that the amino acid sequence of the variant is not identical to any of the amino acid sequences shown in SEQ ID No. 1, SEQ ID No. 2, SEQ ID No. 3 and SEQ ID No. 7, respectively.

5 Claims, 5 Drawing Sheets

```
                10        20        30        40        50        60
                 |         |         |         |         |         |
1  HHNGTNGTMMQYFEWYLPNDGNHWNRLRDDAANLKSKGITAVWIPPAWKGTSQNDVGYGA        60
3  -AAPFNGTMMQYFEWYLPDDGTLWTKVANEANNLSSLGITALWLPPAYKGTSRSDVGYGV        59
2  HHNGTNGTMMQYFEWHLPNDGNHWNRLRDDASNLRNRGITAIWIPPAWKGTSQNDVGYGA        60
4  HHNGTNGTMMQYFEWYLPNDGNHWNRLNSDASNLKSKGITAVWIPPAWKGASQNDVGYGA        60

70        80        90       100       110       120
                 |         |         |         |         |         |
1  YDLYDLGEFNQKGTVRTKYGTRNQLAAVTSLKNNGIQVYGDVVMNHKGGADGTEIVNAV       120
3  YDLYDLGEFNQKGTVRTKYGTKAQYLQAIQAAHAAGMQVYADVVFDHKGGADGTEWVDAV      119
2  YDLYDLGEFNQKGTVRTKYGTRSQLESAIHALKNNGVQVYGDVVMNHKGGADATENVLAV      120
4  YDLYDLGEFNQKGTVRTKYGTRSQLAAVTSLKNNGIQVYGDVVMNHKGGADATEMVRAV       120

130       140       150       160       170       180
                 |         |         |         |         |         |
1  EVNRSNRNQETSGEYAIEAWTKFDFPGRGNNHSSFKWRWYHFDGTDWDQSRQLQNKIYKF      180
3  EVNPSDRNQEISGTYQIQAWTKFDFPGRGNTYSSFKWRWYHFDGVDWDESRKLS-RIYKF      178
2  EVNPNNRNQEISGDYTIEAWTKFDFPGRGNTYSDFKWRWYHFDGVDWDQSRQFQNRIYKF      180
4  EVNPNNRNQEVTGEYTIEAWTRFDFPGRGNTHSSFKWRWYHFDGVDWDQSRRLNNRIYKF      180

190       200       210       220       230       240
                 |         |         |         |         |         |
1  RGTGKAWDWEVDTENGNYDYLMYADVDMDHPEVIHELRNWGVWYTNTLNLDGFRIDAVKH      240
3  RGIGKAWDWEVDTENGNYDYLMYADLDMDHPEVVTELKNWGKWYVNTTNIDGFRLDAVKH      238
2  RGDGKAWDWEVDSENGNYDYLMYADVDMDHPEVVNELRRWGEWYTNTLNLDGFRIDAVKH      240
4  RGHGKAWDWEVDTENGNYDYLMYADIDMDHPEVVNELRNWGVWYTNTLGLDGFRIDAVKH      240

250       260       270       280       290       300
                 |         |         |         |         |         |
1  IKYSFTRDWLTHVRNTTGKPMFAVAEFWKNDLGAIENYLNKTSWNHSAFDVPLHYNLYNA      300
3  IKFSFFPDWLSYVRSQTGKPLFTVGEYWSYDINKLHNYITKTDGTMSLFDAPLHNKFYTA      298
2  IKYSFTRDWLTHVRNATGKEMFAVAEFWKNDLGALENYLNKTNWNHSVFDVPLHYNLYNA      300
4  IKYSFTRDWINHVRSATGKNMFAVAEFWKNDLGAIENYLQKTNWNHSVFDVPLHYNLYNA      300

310       320       330       340       350       360
                 |         |         |         |         |         |
1  SNSGGYYDMRNILNGSVVQKHPTHAVTFVDNHDSQPGEALESFVQQWFKPLAYALVLTRI      360
3  SKSGGAFDMRTLMTNTLMKDQPTLAVTFVDNHDTEPGQALQSWVDPWFKPLAYAFILTRQ      358
2  SNSGGNYDMAKLLNGTVVQKHPMHAVTFVDNHDSQPGESLESFVQEWFKPLAYALILTRE      360
4  SKSGGNYDMRNIFNGTVVQRHPSHAVTFVDNHDSQPEEALESFVEEWFKPLAYALTLTRE      360

370       380       390       400       410       420
                 |         |         |         |         |         |
1  QGYPSVFYGDYYGIPTHGVPAMKSKIDPLLQARQTFAYGTQHDYFDHHDIIGWTREGNSS      420
3  EGYPCVFYGDYYGIPQYNIPSLKSKIDPLLIARRDYAYGTQHDYLDHSDIIGWTREGGTE      418
2  QGYPSVFYGDYYGIPTHSVPAMKAKIDPILEARQNFAYGTQHDYFDHHNIIGWTREGNTT      420
4  QGYPSVFYGDYYGIPTHGVPAMRSKIDPILEARQKYAYGKQNDYLDHHNIIGWTREGNTA      420

430       440       450       460       470       480
                 |         |         |         |         |         |
1  HPNSGLATIMSDGPGGNKWMYVGKNKAGQVWRDITGNRTGTVTINADGWGNFSVNGGSVS      480
3  KPGSGLAALITDGPGGSKWMYVGKQHAGKVFYDLTGNRSDTVTINSDGWGEFKVNGGSVS      478
2  HPNSGLATIMSDGPGGEKWMYVGQNKAGQVWHDITGNKPGTVTINADGWANFSVNGGSVS      480
4  HPNSGLATIMSDGAGGSKWMFVGRNKAGQVWSDITGNRTGTVTINADGWGNFSVNGGSVS      480

490       500       510       520       530       540
                 |         |         |         |         |         |
1  VWVKQ                                                             485
3  VWVPRKTTVSTIARPITTRPWTGEFVRWTEPRLVAW                              514
2  IWVKR                                                             485
4  IWVNK                                                             485
```

Fig. 1

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
       (A) LENGTH: 485 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

```
His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
                20                  25                  30

Asn Leu Lys Ser Lys Gly Ile Thr Ala Val Trp Ile Pro Pro Ala Trp
            35                  40                  45

Lys Gly Thr Ser Gln Asn Asp Val Gly Tyr Gly Ala Tyr Asp Leu Tyr
        50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ser Leu Lys Asn Asn Gly
                    85                  90                  95

Ile Gln Val Tyr Gly Asp Val Val Met Asn His Lys Gly Gly Ala Asp
                100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
        130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                    165                 170                 175

Ile Tyr Lys Phe Arg Gly Thr Gly Lys Ala Trp Asp Trp Glu Val Asp
                180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                    245                 250                 255

Thr Gly Lys Pro Met Phe Ala Val Ala Glu Phe Trp Lys Asn Asp Leu
                260                 265                 270

Gly Ala Ile Glu Asn Tyr Leu Asn Lys Thr Ser Trp Asn His Ser Val
            275                 280                 285

Phe Asp Val Pro Leu His Tyr Asn Leu Tyr Asn Ala Ser Asn Ser Gly
        290                 295                 300

Gly Tyr Tyr Asp Met Arg Asn Ile Leu Asn Gly Ser Val Val Gln Lys
305                 310                 315                 320
```

```
            His Pro Thr His Ala Val Thr Phe Val Asp Asn His Asp Ser Gln Pro
                            325                 330                 335

Gly Glu Ala Leu Glu Ser Phe Val Gln Gln Trp Phe Lys Pro Leu Ala
                            340                 345                 350

Tyr Ala Leu Val Leu Thr Arg Glu Gln Gly Tyr Pro Ser Val Phe Tyr
                            355                 360                 365

Gly Asp Tyr Tyr Gly Ile Pro Thr His Gly Val Pro Ala Met Lys Ser
                            370                 375                 380

Lys Ile Asp Pro Leu Leu Gln Ala Arg Gln Thr Phe Ala Tyr Gly Thr
            385                 390                 395                 400

Gln His Asp Tyr Phe Asp His His Asp Ile Ile Gly Trp Thr Arg Glu
                            405                 410                 415

Gly Asn Ser Ser His Pro Asn Ser Gly Leu Ala Thr Ile Met Ser Asp
                            420                 425                 430

Gly Pro Gly Gly Asn Lys Trp Met Tyr Val Gly Lys Asn Lys Ala Gly
                            435                 440                 445

Gln Val Trp Arg Asp Ile Thr Gly Asn Arg Thr Gly Thr Val Thr Ile
                            450                 455                 460

Asn Ala Asp Gly Trp Gly Asn Phe Ser Val Asn Gly Ser Val Ser
            465                 470                 475                 480

Val Trp Val Lys Gln
                            485

(2) INFORMATION FOR SEQ ID NO: 2:

(i) SEQUENCE CHARACTERISTICS:
            (A) LENGTH: 485 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 2:

His His Asn Gly Thr Asn Gly Thr Met Met Gln Tyr Phe Glu Trp His
            1               5                   10                  15

Leu Pro Asn Asp Gly Asn His Trp Asn Arg Leu Arg Asp Asp Ala Ser
                            20                  25                  30

Asn Leu Arg Asn Arg Gly Ile Thr Ala Ile Trp Ile Pro Pro Ala Trp
                            35                  40                  45

Lys Gly Thr Ser Gln Asn Asp Val Gly Tyr Gly Ala Tyr Asp Leu Tyr
                            50                  55                  60

Asp Leu Gly Glu Phe Asn Gln Lys Gly Thr Val Arg Thr Lys Tyr Gly
            65                  70                  75                  80

Thr Arg Ser Gln Leu Glu Ser Ala Ile His Ala Leu Lys Asn Asn Gly
                            85                  90                  95

Val Gln Val Tyr Gly Asp Val Val Met Asn His Lys Gly Gly Ala Asp
                            100                 105                 110

Ala Thr Glu Asn Val Leu Ala Val Glu Val Asn Pro Asn Asn Arg Asn
                            115                 120                 125

Gln Glu Ile Ser Gly Asp Tyr Thr Ile Glu Ala Trp Thr Lys Phe Asp
                            130                 135                 140

Phe Pro Gly Arg Gly Asn Thr Tyr Ser Asp Phe Lys Trp Arg Trp Tyr
            145                 150                 155                 160

His Phe Asp Gly Val Asp Trp Asp Gln Ser Arg Gln Phe Gln Asn Arg
                            165                 170                 175
```

-continued

```
Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
            245                 250                 255

Thr Gly Lys Glu Met Phe Ala Val Ala Glu Phe Trp Lys Asn Asp Leu
        260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
        290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
            325                 330                 335

Gly Glu Ser Leu Glu Ser Phe Val Gln Glu Trp Phe Lys Pro Leu Ala
        340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
        370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
            405                 410                 415

Gly Asn Thr Thr His Pro Asn Ser Gly Leu Ala Thr Ile Met Ser Asp
        420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
        450                 455                 460

Asn Ala Asp Gly Trp Ala Asn Phe Ser Val Asn Gly Gly Ser Val Ser
465                 470                 475                 480

Ile Trp Val Lys Arg
            485
```

(2) INFORMATION FOR SEQ ID NO: 3:

(i) SEQUENCE CHARACTERISTICS:
        (A) LENGTH: 514 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30
```

```
Leu Ser Ser Leu Gly Ile Thr Ala Leu Trp Leu Pro Ala Tyr Lys
        35                  40                  45
Gly Thr Ser Arg Ser Asp Val Gly Tyr Val Tyr Asp Leu Tyr Asp
        50                  55                  60
Leu Gly Glu Phe Asn Gln Lys Gly Ala Val Arg Thr Lys Tyr Gly Thr
65                      70                  75                  80
Lys Ala Gln Tyr Leu Gln Ala Ile Gln Ala His Ala Ala Gly Met
                85                  90                  95
Gln Val Tyr Ala Asp Val Val Phe Asp His Lys Gly Gly Ala Asp Gly
                100                 105                 110
Thr Glu Trp Val Asp Ala Val Glu Val Asn Pro Ser Asp Arg Asn Gln
            115                 120                 125
Glu Ile Ser Gly Thr Tyr Gln Ile Gln Ala Trp Thr Lys Phe Asp Phe
            130                 135                 140
Pro Gly Arg Gly Asn Thr Tyr Ser Ser Phe Lys Trp Arg Trp Tyr His
145                     150                 155                 160
Phe Asp Gly Val Asp Trp Asp Glu Ser Arg Lys Leu Ser Arg Ile Tyr
                165                 170                 175
Lys Phe Arg Gly Ile Gly Lys Ala Trp Asp Trp Glu Val Asp Thr Glu
                180                 185                 190
Asn Gly Asn Tyr Asp Tyr Leu Met Tyr Ala Asp Leu Asp Met Asp His
            195                 200                 205
Pro Glu Val Val Thr Glu Leu Lys Ser Trp Gly Lys Trp Tyr Val Asn
            210                 215                 220
Thr Thr Asn Ile Asp Gly Phe Arg Leu Asp Ala Val Lys His Ile Lys
225                 230                 235                 240
Phe Ser Phe Phe Pro Asp Trp Leu Ser Asp Val Arg Ser Gln Thr Gly
                245                 250                 255
Lys Pro Leu Phe Thr Val Gly Glu Tyr Trp Ser Tyr Asp Ile Asn Lys
                260                 265                 270
Leu His Asn Tyr Ile Met Lys Thr Asn Gly Thr Met Ser Leu Phe Asp
            275                 280                 285
Ala Pro Leu His Asn Lys Phe Tyr Thr Ala Ser Lys Ser Gly Gly Thr
            290                 295                 300
Phe Asp Met Arg Thr Leu Met Thr Asn Thr Leu Met Lys Asp Gln Pro
305                 310                 315                 320
Thr Leu Ala Val Thr Phe Val Asp Asn His Asp Thr Glu Pro Gly Gln
                325                 330                 335
Ala Leu Gln Ser Trp Val Asp Pro Trp Phe Lys Pro Leu Ala Tyr Ala
            340                 345                 350
Phe Ile Leu Thr Arg Gln Glu Gly Tyr Pro Cys Val Phe Tyr Gly Asp
            355                 360                 365
Tyr Tyr Gly Ile Pro Gln Tyr Asn Ile Pro Ser Leu Lys Ser Lys Ile
        370                 375                 380
Asp Pro Leu Leu Ile Ala Arg Arg Asp Tyr Ala Tyr Gly Thr Gln His
385                 390                 395                 400
Asp Tyr Leu Asp His Ser Asp Ile Ile Gly Trp Thr Arg Glu Gly Val
                405                 410                 415
Thr Glu Lys Pro Gly Ser Gly Leu Ala Ala Leu Ile Thr Asp Gly Pro
            420                 425                 430
Gly Gly Ser Lys Trp Met Tyr Val Gly Lys Gln His Ala Gly Lys Val
            435                 440                 445
```

```
        Phe Tyr Asp Leu Thr Gly Asn Arg Ser Asp Thr Val Thr Ile Asn Ser
            450                 455                 460

Asp Gly Trp Gly Glu Phe Lys Val Asn Gly Gly Ser Val Ser Val Trp
        465                 470                 475                 480

Val Pro Arg Lys Thr Thr Val Ser Thr Ile Ala Trp Ser Ile Thr Thr
                        485                 490                 495

Arg Pro Trp Thr Asp Glu Phe Val Arg Trp Thr Glu Pro Arg Leu Val
                    500                 505                 510

Ala Trp
```

(2) INFORMATION FOR SEQ ID NO: 4:

(i) SEQUENCE CHARACTERISTICS:
        (A) LENGTH: 1455 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

```
CATCATAATG GAACAAATGG TACTATGATG CAATATTTCG AATGGTATTT GCCAAATGAC      60

GGGAATCATT GGAACAGGTT GAGGGATGAC GCAGCTAACT TAAAGAGTAA AGGGATAACA     120

GCTGTATGGA TCCCACCTGC ATGGAAGGGG ACTTCCCAGA ATGATGTAGG TTATGGAGCC     180

TATGATTTAT ATGATCTTGG AGAGTTTAAC CAGAAGGGGA CGGTTCGTAC AAAATATGGA     240

ACACGCAACC AGCTACAGGC TGCGGTGACC TCTTTAAAAA ATAACGGCAT TCAGGTATAT     300

GGTGATGTCG TCATGAATCA TAAAGGTGGA GCAGATGGTA CGGAAATTGT AAATGCGGTA     360

GAAGTGAATC GGAGCAACCG AAACCAGGAA ACCTCAGGAG AGTATGCAAT AGAAGCGTGG     420

ACAAAGTTTG ATTTTCCTGG AAGAGGAAAT AACCATTCCA GCTTTAAGTG GCGCTGGTAT     480

CATTTTGATG GGACAGATTG GGATCAGTCA CGCCAGCTTC AAAACAAAAT ATATAAATTC     540

AGGGGAACAG GCAAGGCCTG GGACTGGGAA GTCGATACAG AGAATGGCAA CTATGACTAT     600

CTTATGTATG CAGACGTGGA TATGGATCAC CCAGAAGTAA TACATGAACT TAGAAACTGG     660

GGAGTGTGGT ATACGAATAC ACTGAACCTT GATGGATTTA GAATAGATGC AGTGAAACAT     720

ATAAAATATA GCTTTACGAG AGATTGGCTT ACACATGTGC GTAACACCAC AGGTAAACCA     780

ATGTTTGCAG TGGCTGAGTT TTGGAAAAAT GACCTTGGTG CAATTGAAAA CTATTTGAAT     840

AAAACAAGTT GGAATCACTC GGTGTTTGAT GTTCCTCTCC ACTATAATTT GTACAATGCA     900

TCTAATAGCG GTGGTTATTA TGATATGAGA AATATTTTAA ATGGTTCTGT GGTGCAAAAA     960

CATCCAACAC ATGCCGTTAC TTTTGTTGAT AACCATGATT CTCAGCCCGG GGAAGCATTG    1020

GAATCCTTTG TTCAACAATG GTTTAAACCA CTTGCATATG CATTGGTTCT GACAAGGGAA    1080

CAAGGTTATC CTTCCGTATT TTATGGGGAT TACTACGGTA TCCCAACCCA TGGTGTTCCG    1140

GCTATGAAAT CTAAAATAGA CCCTCTTCTG CAGGCACGTC AAACTTTTGC CTATGGTACG    1200

CAGCATGATT ACTTTGATCA TCATGATATT ATCGGTTGGA CAAGAGAGGG AAATAGCTCC    1260

CATCCAAATT CAGGCCTTGC CACCATTATG TCAGATGGTC CAGGTGGTAA CAAATGGATG    1320

TATGTGGGGA AAAATAAAGC GGGACAAGTT TGGAGAGATA TTACCGGAAA TAGGACAGGC    1380

ACCGTCACAA TTAATGCAGA CGGATGGGGT AATTTCTCTG TTAATGGAGG GTCCGTTTCG    1440

GTTTGGGTGA AGCAA                                                    1455
```

(2) INFORMATION FOR SEQ ID NO: 5:

(i) SEQUENCE CHARACTERISTICS:
    (A) LENGTH: 1455 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 5:

```
CATCATAATG GGACAAATGG GACGATGATG CAATACTTTG AATGGCACTT GCCTAATGAT     60
GGGAATCACT GGAATAGATT AAGAGATGAT GCTAGTAATC TAAGAAATAG AGGTATAACC    120
GCTATTTGGA TTCCGCCTGC CTGGAAAGGG ACTTCGCAAA ATGATGTGGG GTATGGAGCC    180
TATGATCTTT ATGATTTAGG GGAATTTAAT CAAAAGGGGA CGGTTCGTAC TAAGTATGGG    240
ACACGTAGTC AATTGGAGTC TGCCATCCAT GCTTTAAAGA ATAATGGCGT TCAAGTTTAT    300
GGGGATGTAG TGATGAACCA TAAAGGAGGA GCTGATGCTA CAGAAAACGT TCTTGCTGTC    360
GAGGTGAATC CAAATAACCG GAATCAAGAA ATATCTGGGG ACTACACAAT TGAGGCTTGG    420
ACTAAGTTTG ATTTTCCAGG GAGGGTAAT ACATACTCAG ACTTTAAATG GCGTTGGTAT    480
CATTTCGATG GTGTAGATTG GGATCAATCA CGACAATTCC AAAATCGTAT CTACAAATTC    540
CGAGGTGATG GTAAGGCATG GGATTGGGAA GTAGATTCGG AAAATGGAAA TTATGATTAT    600
TTAATGTATG CAGATGTAGA TATGGATCAT CCGGAGGTAG TAAATGAGCT TAGAAGATGG    660
GGAGAATGGT ATACAAATAC ATTAAATCTT GATGGATTTA GGATCGATGC GGTGAAGCAT    720
ATTAAATATA GCTTTACACG TGATTGGTTG ACCCATGTAA GAAACGCAAC GGGAAAAGAA    780
ATGTTTGCTG TTGCTGAATT TTGGAAAAAT GATTTAGGTG CCTTGGAGAA CTATTTAAAT    840
AAAACAAACT GGAATCATTC TGTCTTTGAT GTCCCCCTTC ATTATAATCT TTATAACGCG    900
TCAAATAGTG GAGGCAACTA TGACATGGCA AAACTTCTTA ATGGAACGGT TGTTCAAAAG    960
CATCCAATGC ATGCCGTAAC TTTTGTGGAT AATCACGATT CTCAACCTGG GGAATCATTA   1020
GAATCATTTG TACAAGAATG GTTTAAGCCA CTTGCTTATG CGCTTATTTT AACAAGAGAA   1080
CAAGGCTATC CCTCTGTCTT CTATGGTGAC TACTATGGAA TTCCAACACA TAGTGTCCCA   1140
GCAATGAAAG CCAAGATTGA TCCAATCTTA GAGGCGCGTC AAAATTTTGC ATATGGAACA   1200
CAACATGATT ATTTTGACCA TCATAATATA ATCGGATGGA CACGTGAAGG AAATACCACG   1260
CATCCCAATT CAGGACTTGC GACTATCATG TCGGATGGGC CAGGGGGAGA GAAATGGATG   1320
TACGTAGGGC AAAATAAAGC AGGTCAAGTT TGGCATGACA TAACTGGAAA TAAACCAGGA   1380
ACAGTTACGA TCAATGCAGA TGGATGGGCT AATTTTTCAG TAAATGGAGG ATCTGTTTCC   1440
ATTTGGGTGA AACGA                                                   1455
```

(2) INFORMATION FOR SEQ ID NO: 6:

(i) SEQUENCE CHARACTERISTICS:
    (A) LENGTH: 1548 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 6:

```
GCCGCACCGT TTAACGGCAC CATGATGCAG TATTTTGAAT GGTACTTGCC GGATGATGGC     60
ACGTTATGGA CCAAAGTGGC CAATGAAGCC AACAACTTAT CCAGCCTTGG CATCACCGCT    120
CTTTGGCTGC CGCCCGCTTA CAAAGGAACA AGCCGCAGCG ACGTAGGGTA CGGAGTATAC    180
```

```
GACTTGTATG ACCTCGGCGA ATTCAATCAA AAAGGGACCG TCCGCACAAA ATACGGAACA      240

AAAGCTCAAT ATCTTCAAGC CATTCAAGCC GCCCACGCCG CTGGAATGCA AGTGTACGCC      300

GATGTCGTGT TCGACCATAA AGGCGGCGCT GACGGCACGG AATGGGTGGA CGCCGTCGAA      360

GTCAATCCGT CCGACCGCAA CCAAGAAATC TCGGGCACCT ATCAAATCCA AGCATGGACG      420

AAATTTGATT TTCCCGGGCG GGCAACACCC TACTCCAGCT TTAAGTGGCG CTGGTACCAT      480

TTTGACGGCG TTGATTGGGA CGAAAGCCGA AAATTGAGCC GCATTTACAA ATTCCGCGGC      540

ATCGGCAAAG CGTGGGATTG GGAAGTAGAC ACGGAAAACG GAAACTATGA CTACTTAATG      600

TATGCCGACC TTGATATGGA TCATCCCGAA GTCGTGACCG AGCTGAAAAA CTGGGGGAAA      660

TGGTATGTCA ACACAACGAA CATTGATGGG TTCCGGCTTG ATGCCGTCAA GCATATTAAG      720

TTCAGTTTTT TTCCTGATTG GTTGTCGTAT GTGCGTTCTC AGACTGGCAA GCCGCTATTT      780

ACCGTCGGGG AATATTGGAG CTATGACATC AACAAGTTGC ACAATTACAT TACGAAAACA      840

GACGGAACGA TGTCTTTGTT TGATGCCCCG TTACACAACA AATTTTATAC CGCTTCCAAA      900

TCAGGGGGCG CATTTGATAT GCGCACGTTA ATGACCAATA CTCTCATGAA AGATCAACCG      960

ACATTGGCCG TCACCTTCGT TGATAATCAT GACACCGAAC CCGGCCAAGC GCTGCAGTCA     1020

TGGGTCGACC CATGGTTCAA ACCGTTGGCT TACGCCTTTA TTCTAACTCG GCAGGAAGGA     1080

TACCCGTGCG TCTTTTATGG TGACTATTAT GGCATTCCAC AATATAACAT TCCTTCGCTG     1140

AAAAGCAAAA TCGATCCGCT CCTCATCGCG CGCAGGGATT ATGCTTACGG AACGCAACAT     1200

GATTATCTTG ATCACTCCGA CATCATCGGG TGGACAAGGG AAGGGGGCAC TGAAAAACCA     1260

GGATCCGGAC TGGCCGCACT GATCACCGAT GGGCCGGGAG GAAGCAAATG GATGTACGTT     1320

GGCAAACAAC ACGCTGGAAA AGTGTTCTAT GACCTTACCG GCAACCGGAG TGACACCGTC     1380

ACCATCAACA GTGATGGATG GGGGGAATTC AAAGTCAATG GCGGTTCGGT TTCGGTTTGG     1440

GTTCCTAGAA AAACGACCGT TTCTACCATC GCTCGGCCGA TCACAACCCG ACCGTGGACT     1500

GGTGAATTCG TCCGTTGGAC CGAACCACGG TTGGTGGCAT GGCCTTGA                  1548
```

(2) INFORMATION FOR SEQ ID NO: 7:

(i) SEQUENCE CHARACTERISTICS:
        (A) LENGTH: 485 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
His His Asn Gly Thr Asn Gly Thr Met Met Gln Tyr Phe Glu Trp Tyr
 1               5                  10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
```

```
                  100                 105                 110
    Ala Thr Glu Met Val Arg Ala Val Glu Val Asn Pro Asn Asn Arg Asn
                115                 120                 125
    Gln Glu Val Thr Gly Glu Tyr Thr Ile Glu Ala Trp Thr Arg Phe Asp
                130                 135                 140
    Phe Pro Gly Arg Gly Asn Thr His Ser Ser Phe Lys Trp Arg Trp Tyr
    145                 150                 155                 160
    His Phe Asp Gly Val Asp Trp Asp Gln Ser Arg Arg Leu Asn Asn Arg
                    165                 170                 175
    Ile Tyr Lys Phe Arg Gly His Gly Lys Ala Trp Asp Trp Glu Val Asp
                180                 185                 190
    Thr Glu Asn Gly Asn Tyr Asp Tyr Leu Met Tyr Ala Asp Ile Asp Met
                195                 200                 205
    Asp His Pro Glu Val Val Asn Glu Leu Arg Asn Trp Gly Val Trp Tyr
    210                 215                 220
    Thr Asn Thr Leu Gly Leu Asp Gly Phe Arg Ile Asp Ala Val Lys His
    225                 230                 235                 240
    Ile Lys Tyr Ser Phe Thr Arg Asp Trp Ile Asn His Val Arg Ser Ala
                245                 250                 255
    Thr Gly Lys Asn Met Phe Ala Val Ala Glu Phe Trp Lys Asn Asp Leu
                260                 265                 270
    Gly Ala Ile Glu Asn Tyr Leu Gln Lys Thr Asn Trp Asn His Ser Val
                275                 280                 285
    Phe Asp Val Pro Leu His Tyr Asn Leu Tyr Asn Ala Ser Lys Ser Gly
                290                 295                 300
    Gly Asn Tyr Asp Met Arg Asn Ile Phe Asn Gly Thr Val Val Gln Arg
    305                 310                 315                 320
    His Pro Ser His Ala Val Thr Phe Val Asp Asn His Asp Ser Gln Pro
                    325                 330                 335
    Glu Glu Ala Leu Glu Ser Phe Val Glu Glu Trp Phe Lys Pro Leu Ala
                340                 345                 350
    Tyr Ala Leu Thr Leu Thr Arg Glu Gln Gly Tyr Pro Ser Val Phe Tyr
                355                 360                 365
    Gly Asp Tyr Tyr Gly Ile Pro Thr His Gly Val Pro Ala Met Arg Ser
    370                 375                 380
    Lys Ile Asp Pro Ile Leu Glu Ala Arg Gln Lys Tyr Ala Tyr Gly Lys
    385                 390                 395                 400
    Gln Asn Asp Tyr Leu Asp His His Asn Ile Ile Gly Trp Thr Arg Glu
                    405                 410                 415
    Gly Asn Thr Ala His Pro Asn Ser Gly Leu Ala Thr Ile Met Ser Asp
                420                 425                 430
    Gly Ala Gly Gly Ser Lys Trp Met Phe Val Gly Arg Asn Lys Ala Gly
                435                 440                 445
    Gln Val Trp Ser Asp Ile Thr Gly Asn Arg Thr Gly Thr Val Thr Ile
                450                 455                 460
    Asn Ala Asp Gly Trp Gly Asn Phe Ser Val Asn Gly Gly Ser Val Ser
    465                 470                 475                 480
    Ile Trp Val Asn Lys
                485

(2) INFORMATION FOR SEQ ID NO:8:

(i) SEQUENCE CHARACTERISTICS:
        (A) LENGTH: 30 base pairs
```

(B) TYPE: nucleic acid
(C) STRANDEDNESS: single
(D) TOPOLOGY: linear (xi) SEQUENCE DESCRIPTION: SEQ ID NO:8:

GCTGCGGTGA CCTCTTTAAA AAATAACGGC                30

(2) INFORMATION FOR SEQ ID NO:9:

(i) SEQUENCE CHARACTERISTICS:
(A) LENGTH: 24 base pairs
(B) TYPE: nucleic acid
(C) STRANDEDNESS: single
(D) TOPOLOGY: linear (xi) SEQUENCE DESCRIPTION: SEQ ID NO:9:

CCACCGCTAT TAGATGCATT GTAC                      24

(2) INFORMATION FOR SEQ ID NO:10:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:10:

CTTACGTATG CAGACGTCGA TATGGATCAC CC              32

(2) INFORMATION FOR SEQ ID NO:11:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:11:

GATCCATATC GACGTCTGCA TACGTAAGAT AGTC            34

(2) INFORMATION FOR SEQ ID NO:12:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:12:

TTASGGGCAA GGCCTGGGAC TGG                       23

(2) INFORMATION FOR SEQ ID NO:13:

(i) SEQUENCE CHARACTERISTICS:
(A) LENGTH: 37 base pairs
(B) TYPE: nucleic acid
(C) STRANDEDNESS: single
(D) TOPOLOGY: linear (xi) SEQUENCE DESCRIPTION: SEQ ID NO:13:

CCCAGGCCTT GCCCSTAAAT TTATATATTT TGTTTTG        37

(2) INFORMATION FOR SEQ ID NO:14:

(i) SEQUENCE CHARACTERISTICS:
(A) LENGTH: 31 base pairs
(B) TYPE: nucleic acid

```
        (C) STRANDEDNESS: single
        (D) TOPOLOGY: linear (xi) SEQUENCE DESCRIPTION: SEQ ID NO:14:

GGTTTCGGTT CGAAGGATTC ACTTCTACCG C                                          31

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:15:

GCGGTAGAAG TGAATCCTTC GAACCGAAAC CAG                                        33

(2) INFORMATION FOR SEQ ID NO:16:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:16:

GGTACTATCG TAACAATGGC CGATTGCTGA CGCTGTTATT TGC                             43

(2) INFORMATION FOR SEQ ID NO:17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:17:

CTGTGACTGG TGAGTACTCA ACCAAGTC                                              28

(2) INFORMATION FOR SEQ ID NO:18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:18:

CTACTTCCCA ATCCCAAGCT TTACCTCGGA ATTTG                                      35

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:19:

CAAATTCCGA GGTAAAGCTT GGGATTGGGA AGTAG                                      35

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
```

(D) TOPOLOGY: linear (xi) SEQUENCE DESCRIPTION: SEQ ID NO:20:

TTGAACAACC GTTCCATTAA GAAG                                                24

(2) INFORMATION FOR SEQ ID NO:21:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:21:

CTCTGTATCG ACTTCCCAGT CCCAAGCTTT TGTCCTGAAT TTATATATTT TGTTTTGAAG        60

(2) INFORMATION FOR SEQ ID NO:22:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (xi) SEQUENCE DESCRIPTION: SEQ ID NO:22:

CTCTGTATCG ACTTCCCAGT CCCAAGCTTT GCCTCCGAAT TTATATATTT TGTTTTGAAG        60

(2) INFORMATION FOR SEQ ID NO:23:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (xi) SEQUENCE DESCRIPTION: SEQ ID NO:23:

ATGTGTAAGC CAATCGCGAG TAAAGCTAAA TTTTATATGT TTCACTGCAT C                 51

(2) INFORMATION FOR SEQ ID NO:24:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO:24:

GCACCAAGGT CATTTCGCCA GAATTCAGCC ACTG                                    34

(2) INFORMATION FOR SEQ ID NO:25:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (xi) SEQUENCE DESCRIPTION: SEQ ID NO:25:

TGTCAGAACC AACGCGTATG CACATGGTTT AAACCATTG                               39

(2) INFORMATION FOR SEQ ID NO:26:

(i) SEQUENCE CHARACTERISTICS:
            (A) LENGTH: 42 base pairs
            (B) TYPE: nucleic acid
            (C) STRANDEDNESS: single
            (D) TOPOLOGY: linear (xi) SEQUENCE DESCRIPTION: SEQ ID NO:26:

ACCACCTGGA CCATCGCTGC AGATGGTGGC AAGGCCTGAA TT                42

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:27:

GGCAAAAGTT TGACGTGCCT CGAGAAGAGG GTCTAT                       36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:28:

TTGTCCCGCT TTATTCTGGC CAACATACAT CCATTT                       36

(2) INFORMATION FOR SEQ ID NO:29:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:29:

CCCAATCCCA AGCTTTACCA YCGAACTTGT AGATACG                      37

(2) INFORMATION FOR SEQ ID NO:30:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:30:

CCCAATCCCA AGCTTTATCT CSGAACTTGT AGATACG                      37

(2) INFORMATION FOR SEQ ID NO:31:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:31:

GATCCATATC GACGTCTGCA TACAGTAAAT AATC                         34

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear

```
           (ii) MOLECULE TYPE: cDNA (xi) SEQUENCE DESCRIPTION: SEQ ID NO:32:

GATCCATATC GACGTCTGCA TAAATTAAAT AATC                                    34
```

AMYLASE VARIANTS

This application is a continuation of international application PCT/DK96/00056, filed Feb. 5, 1996.

FIELD OF THE INVENTION

The present invention relates to α-amylase variants having improved properties relative to the parent enzyme (e.g. improved thermal and/or oxidation stability and/or reduced calcium ion dependency), and thereby improved washing and/or dishwashing (and/or textile desizing) performance. The invention also relates to DNA constructs encoding the variants, and to vectors and cells harboring the DNA constructs. The invention further relates to methods of producing the amylase variants, and to detergent additives and detergent compositions comprising the amylase variants. Furthermore, the invention relates to the use of the amylase variants for textile desizing.

BACKGROUND OF THE INVENTION

α-Amylase enzymes have been used industrially for a number of years and for a variety of different purposes, the most important of which are starch liquefaction, textile desizing, starch modification in the paper and pulp industry, and for brewing and baking. A further use of α-amylases which is becoming increasingly important is the removal of starchy stains during washing or dishwashing.

In recent years attempts have been made to construct α-amylase variants having improved properties with respect to specific uses such as starch liquefaction and textile desizing.

For instance, U.S. Pat. No. 5,093,257 discloses chimeric α-amylases comprising an N-terminal part of a *B. stearothermophilus* α-amylase and a C-terminal part of a *B. licheniformis* α-amylase. The chimeric α-amylases are stated to have unique properties, such as a different thermostability, as compared to their parent α-amylase. However, all of the specifically described chimeric α-amylases were shown to have a decreased enzymatic activity as compared to their parent α-amylases.

EP 252 666 describes hybrid amylases of the general formula Q-R-L, in which Q is a N-terminal polypeptide residue of from 55 to 60 amino acid residues which is at least 75% homologous to the 57 N-terminal amino acid residues of a specified α-amylase from *B. amyloliquefaciens*, R is a specified polypeptide, and L is a C-terminal polypeptide comprising from 390 to 400 amino acid residues which is at least 75% homologous to the 395 C-terminal amino acid residues of a specified *B. licheniformis* α-amylase.

Suzuki et al. (1989) disclose chimeric α-amylases, in which specified regions of a *B. amyloliquefaciens* α-amylase have been substituted for the corresponding regions of a *B. licheniformis* α-amylase. The chimeric α-amylases were constructed with the purpose of identifying regions responsible for thermostability. Such regions were found to include amino acid residues 177–186 and amino acid residues 255–270 of the *B. amyloliquefaciens* α-amylase. The alterations of amino acid residues in the chimeric α-amylases did not seem to affect properties of the enzymes other than their thermostability.

WO 91/00353 discloses α-amylase mutants which differ from their parent α-amylase in at least one amino acid residue. The α-amylase mutants disclosed in said patent application are stated to exhibit improved properties for application in the degradation of starch and/or textile desizing due to their amino acid substitutions. Some of the mutants exhibit improved stability, but no improvements in enzymatic activity were reported or indicated. The only mutants exemplified are prepared from a parent *B. licheniformis* α-amylase and carry one of the following mutations: H133Y or H133Y+T149I. Another suggested mutation is A111T.

FR 2,676,456 discloses mutants of the *B. licheniformis* α-amylase, in which an amino acid residue in the proximity of His 133 and/or an amino acid residue in the proximity of Ala 209 have been replaced by a more hydrophobic amino acid residue. The resulting α-amylase mutants are stated to have an improved thermostability and to be useful in the textile, paper, brewing and starch liquefaction industry.

EP 285 123 discloses a method of performing random mutagenesis of a nucleotide sequence. As an example of such sequence a nucleotide sequence encoding a *B. stearothermophilus* α-amylase is mentioned. When mutated, an α-amylase variant having improved activity at low pH values is obtained.

In none of the above references is it mentioned or even suggested that α-amylase mutants may be constructed which have improved properties with respect to the detergent industry.

EP525 610 relates to mutant enzymes having improved stability towards ionic tensides (surfactants). The mutant enzymes have been produced by replacing an amino acid residue in the surface part of the parent enzyme with another amino acid residue. The only mutant enzyme specifically described in EP 525 610 is a protease. Amylase is mentioned as an example of an enzyme which may obtain an improved stability towards ionic tensides, but the type of amylase, its origin or specific mutations are not specified.

WO 94/02597 discloses α-amylase mutants which exhibit improved stability and activity in the presence of oxidizing agents. In the mutant α-amylases, one or more methionine residues have been replaced with amino acid residues different from Cys and Met. The α-amylase mutants are stated to be useful as detergent and/or dishwashing additives as well as for textile desizing.

WO 94/18314 discloses oxidatively stable α-amylase mutants, including mutations in the M197 position of *B. licheniformis* α-amylase.

EP 368 341 describes the use of pullulanase and other amylolytic enzymes optionally in combination with an α-amylase for washing and dishwashing.

An object of the present invention is to provide α-amylase variants which—relative to their parent α-amylase—possess improved properties of importance, inter alia, in relation to the washing and/or dishwashing performance of the variants in question, e.g. increased thermal stability, increased stability towards oxidation, reduced dependency on $Ca^{2+}$ ion and/or improved stability or activity in the pH region of relevance in, e.g., laundry washing or dishwashing. Such variant α-amylases have the advantage, among others, that they may be employed in a lower dosage than their parent α-amylase. Furthermore, the α-amylase variants may be able to remove starchy stains which cannot, or can only with difficulty, be removed by α-amylase detergent enzymes known today.

BRIEF DISCLOSURE OF THE INVENTION

A goal of the work underlying the present invention was to improve, if possible, the stability of, inter alia, particular α-amylases which are obtainable from Bacillus strains and which themselves had been selected on the basis of their starch removal performance in alkaline media (such as in detergent solutions as typically employed in laundry washing or dishwashing) relative to many of the currently commercially available α-amylases. In this connection, the present inventors have surprisingly found that it is in fact possible to improve properties of the types mentioned earlier (vide supra) of such a parent α-amylase by judicial modification of one or more amino acid residues in various regions of the amino acid sequence of the parent α-amylase. The present invention is based on this finding.

Accordingly, in a first aspect the present invention relates to variants of a parent α-amylase, the parent α-amylase in question being one which:

i) has one of the amino acid sequences shown in SEQ ID No. 1, SEQ ID No. 2, SEQ ID No. 3 and SEQ ID No. 7, respectively, herein; or ii) displays at least 80% homology with one or more of the amino acid sequences shown in SEQ ID No. 1, SEQ ID No. 2, SEQ ID No. 3 and SEQ ID No. 7; and/or displays immunological cross-reactivity with an antibody raised against an α-amylase having one of the amino acid sequences shown in SEQ ID No. 1, SEQ ID No. 2, SEQ ID No. 3 and SEQ ID No. 7, respectively; and/or is encoded by a DNA sequence which hybridizes with the same probe as a DNA sequence encoding an α-amylase having one of the amino acid sequences shown in SEQ ID No. 1, SEQ ID No. 2, SEQ ID No. 3 and SEQ ID No. 7, respectively.

An α-amylase variant of the invention is subject to the proviso that it is a variant which does not have an amino acid sequence identical to the amino acid sequence shown in SEQ ID No. 1, in SEQ ID No. 2, in SEQ ID No. 3 or in SEQ ID No. 7.

DNA sequences encoding the first three of the α-amylase amino acid sequences in question are shown in SEQ ID No. 4 (encoding the amino acid sequence shown in SEQ ID No. 1), SEQ ID No. 5 (encoding the amino acid sequence shown in SEQ ID No. 2) and SEQ ID No. 6 (encoding the amino acid sequence shown in SEQ ID No. 3).

The amino acid sequences of the SEQ ID No. 1 and SEQ ID No. 2 parent α-amylases, and the corresponding DNA sequences (SEQ ID No. 4 and SEQ ID No. 5, respectively) are also disclosed in WO 95/26397 (under the same SEQ ID Nos. as in the present application).

The variants of the invention are variants in which: (a) at least one amino acid residue of the parent α-amylase has been deleted; and/or (b) at least one amino acid residue of the parent α-amylase has been replaced (i.e. substituted) by a different amino acid residue; and/or (c) at least one amino acid residue has been inserted relative to the parent α-amylase. The variants in question have themselves α-amylase activity and exhibit at least one of the following properties relative to the parent α-amylase:

increased thermostability, i.e. satisfactory retention of enzymatic activity at a temperature higher than that suitable for use with the parent enzyme;

increased oxidation stability, i.e. increased resistance to degradation by oxidants (such as oxygen, oxidizing bleaching agents and the like);

reduced $Ca^{2+}$ dependency, i.e. the ability to function satisfactorily in the presence of a lower $Ca^{2+}$ concentration than in the case of the parent α-amylase. α-Amylases with such reduced $Ca^{2+}$ dependency are highly desirable for use in detergent compositions, since such compositions typically contain relatively large amounts of substances (such as phosphates, EDTA and the like) which bind calcium ions strongly.

Examples of other desirable improvements or modifications of properties (relative to the parent α-amylase in question) which may be achieved with a variant according to the invention are:

increased stability and/or α-amylolytic activity at neutral to relatively high pH values, e.g. at pH values in the range of 7–10.5, such as in the range of 8.5–10.5;

increased α-amylolytic activity at relatively high temperatures, e.g. temperatures in the range of 40–70° C.;

increase or decrease of the isoelectric point (pI) so as to better match the pI value for the α-amylase variant in question to the pH of the medium (e.g. a laundry washing medium, dishwashing medium or textile-desizing medium) in which the variant is to be employed (vide infra); and improved binding of a particular type of substrate, improved specificity towards a substrate, and/or improved specificity with respect to cleavage (hydrolysis) of substrate.

An amino acid sequence is considered to be X% homologous to the parent α-amylase if a comparison of the respective amino acid sequences, performed via known algorithms, such as the one described by Lipman and Pearson in *Science* 227 (1985) p. 1435, reveals an identity of X%. The GAP computer program from the GCG package, version 7.3 (June 1993), may suitably be used, employing default values for GAP penalties [Genetic Computer Group (1991) Programme Manual for the GCG Package, version 7, 575 Science Drive, Madison, Wis., USA 53711].

In the context of the present invention, "improved performance" as used in connection with washing and dishwashing is, as already indicated above, intended to mean improved removal of starchy stains, i.e. stains containing starch, during washing or dishwashing, respectively. The performance may be determined in conventional washing and dishwashing experiments and the improvement evaluated as a comparison with the performance of the parent α-amylase in question. An example of a small-scale "mini dishwashing test" which can be used an indicator of dishwashing performance is described in the Experimental section, below.

It will be understood that a variety of different characteristics of an α-amylase variant, including specific activity, substrate specificity, $K_m$ (the so-called "Michaelis constant" in the Michaelis-Menten equation), $V_{max}$ [the maximum rate (plateau value) of conversion of a given substrate determined on the basis of the Michaelis-Menten equation], pI, pH optimum, temperature optimum, thermoactivation, stability towards oxidants or surfactants (e.g. in detergents), etc., taken alone or in combination, can contribute to improved performance. The skilled person will be aware that the performance of the variant cannot, alone, be predicted on the basis of the above characteristics, but would have to be accompanied by washing and/or dishwashing performance tests.

In further aspects the invention relates to a DNA construct comprising a DNA sequence encoding an α-amylase variant of the invention, a recombinant expression vector carrying the DNA construct, a cell which is transformed with the DNA construct or the vector, as well as a method of producing an α-amylase variant by culturing such a cell under conditions conducive to the production of the α-amylase variant, after which the α-amylase variant is recovered from the culture.

In a further aspect the invention relates to a method of preparing a variant of a parent α-amylase which by virtue of its improved properties as described above exhibits improved washing and/or dishwashing performance as compared to the parent α-amylase. This method comprises
  a) constructing a population of cells containing genes encoding variants of said parent α-amylase,
  b) screening the population of cells for α-amylase activity under conditions simulating at least one washing and/or dishwashing condition,
  c) isolating a cell from the population containing a gene encoding a variant of said parent α-amylase which has improved activity as compared with the parent α-amylase under the conditions selected in step b),
  d) culturing the cell isolated in step c) under suitable conditions in an appropriate culture medium, and
  e) recovering the α-amylase variant from the culture obtained in step d).

The invention also relates to a variant (which is a variant according the invention) prepared by the latter method.

In the present context, the term "simulating at least one washing and/or dishwashing condition" is intended to indicate a simulation of, e.g., the temperature or pH prevailing during washing or dishwashing, or of the chemical composition of a detergent composition to be used in the washing or dishwashing treatment. The term "chemical composition" is intended to include one, or a combination of two or more, constituents of the detergent composition in question. The constituents of a number of different detergent compositions are listed further below.

The "population of cells" referred to in step a) may suitably be constructed by cloning a DNA sequence encoding a parent α-amylase and subjecting the DNA to site-directed or random mutagenesis as described herein.

In the present context the term "variant" is used interchangeably with the term "mutant". The term "variant" is intended to include hybrid α-amylases, i.e. α-amylases comprising parts of at least two different α-amylolytic enzymes. Thus, such a hybrid may be constructed, e.g., from: one or more parts each deriving from a variant as already defined above; or one or more parts each deriving from a variant as already defined above, and one or more parts each deriving from an unmodified parent α-amylase. In this connection, the invention also relates to a method of producing such a hybrid α-amylase having improved washing and/or dishwashing performance as compared to any of its constituent enzymes (i.e. as compared to any of the enzymes which contribute a part to the hybrid), which method comprises:
  a) recombining in vivo or in vitro the N-terminal coding region of an α-amylase gene or corresponding cDNA of one of the constituent α-amylases with the C-terminal coding region of an α-amylase gene or corresponding cDNA of another constituent α-amylase to form recombinants,
  b) selecting recombinants that produce a hybrid α-amylase having improved washing and/or dishwashing performance as compared to any of its constituent α-amylases,
  c) culturing recombinants selected in step b) under suitable conditions in an appropriate culture medium, and
  d) recovering the hybrid α-amylase from the culture obtained in step c).

In further aspects the invention relates to the use of an α-amylase variant of the invention [including any variant or hybrid prepared by one of the above mentioned methods] as a detergent enzyme, in particular for washing or dishwashing, to a detergent additive and a detergent composition comprising the α-amylase variant, and to the use of an α-amylase variant of the invention for textile desizing.

Random mutagenesis may be used to generate variants according to the invention, and the invention further relates to a method of preparing a variant of a parent α-amylase, which method comprises
  (a) subjecting a DNA sequence encoding the parent α-amylase to random mutagenesis,
  (b) expressing the mutated DNA sequence obtained in step (a) in a host cell, and
  (c) screening for host cells expressing a mutated amylolytic enzyme which has improved properties as described above (e.g. properties such as decreased calcium dependency, increased oxidation stability, increased thermostability, and/or improved activity at relatively high pH) as compared to the parent α-amylase.

DETAILED DISCLOSURE OF THE INVENTION
Nomenclature
In the present description and claims, the conventional one-letter codes for nucleotides and the conventional one-letter and three-letter codes for amino acid residues are used. For ease of reference, α-amylase variants of the invention are described by use of the following nomenclature:

Original amino acid(s):position(s):substituted amino acid(s)

According to this nomenclature, and by way of example, the substitution of alanine for asparagine in position 30 is shown as:
  Ala 30 Asn or A30N
a deletion of alanine in the same position is shown as:
  Ala 30 * or A30*
and insertion of an additional amino acid residue, such as lysine, is shown as:
  Ala 30 AlaLys or A30AK
A deletion of a consecutive stretch of amino acid residues, exemplified by amino acid residues 30-33, is indicated as (30-33)*.

Where a specific α-amylase contains a "deletion" (i.e. lacks an amino acid residue) in comparison with other α-amylases and an insertion is made in such a position, this is indicated as:
  * 36 Asp or *36D
for insertion of an aspartic acid in position 36.

Multiple mutations are separated by plus signs, i.e.:
  Ala 30 Asp+Glu 34 Ser or A30N+E34S
representing mutations in positions 30 and 34 (in which alanine and glutamic acid replace, i.e. are substituted for, asparagine and serine, respectively).

When one or more alternative amino acid residues may be inserted in a given position this is indicated as:
  A30N,E or
  A30N or A30E Furthermore, when a position suitable for modification is identified herein without any specific modification being suggested, it is to be understood that any other amino acid residue may be substituted for the amino acid residue present in that position (i.e. any amino acid residue—other than that normally present in the position in question—chosen among A, R, N, D, C, Q, E, G, H, I, L, K, M, F, P, S, T, W, Y and V). Thus, for instance, when a modification (replacement) of a methionine in position 202 is mentioned, but not specified, it is to be understood that any of the other amino acids may be substituted for the methionine, i.e. any other amino acid chosen among A,R,N,D,C,Q,E,G,H,I,L,K, F,P,S,T,W,Y and V.

The Parent α-amylase

As already indicated, an α-amylase variant of the invention is very suitably prepared on the basis of a parent α-amylase having one of the amino acid sequences shown in SEQ ID No. 1, SEQ ID No. 2, SEQ ID No. 3 and SEQ ID No. 7, respectively (vide infra).

The parent α-amylases having the amino acid sequences shown in SEQ ID No. 1 and SEQ ID No. 2, respectively, are obtainable from alkalophilic Bacillus strains (strain NCIB 12512 and strain NCIB 12513, respectively), both of which are described in detail in EP 0 277 216 B1. The preparation, purification and sequencing of these two parent α-amylases is described in WO 95/26397 [see the Experimental section herein (vide infra)].

The parent α-amylase having the amino acid sequence shown in SEQ ID No. 3 is obtainable from *Bacillus stearothermophilus* and is described in, inter alia, *J. Bacteriol.* 166 (1986) pp. 635–643.

The parent α-amylase having the amino acid sequence shown in SEQ ID No. 7 (which is the same sequence as that numbered 4 in FIG. 1) is obtainable from a "Bacillus sp. #707" and is described by Tsukamoto et al. in *Biochem. Biophys. Res. Commun.* 151 (1988) pp. 25–31.

Apart from variants of the above-mentioned parent α-amylases having the amino acid sequences shown in SEQ ID No. 1, SEQ ID No. 2, SEQ ID No. 3 and SEQ ID No. 7, respectively, other interesting variants according to the invention include variants of parent α-amylases which have amino acid sequences exhibiting a high degree of homology, such as at least 70% homology, preferably (as already indicated) at least 80% homology, desirably at least 85% homology, and more preferably at least 90% homology, e.g. ≧95% homology, with at least one of the latter four amino acid sequences.

As also already indicated above, further criteria for identifying a suitable parent α-amylase are a) that the α-amylase displays an immunological cross-reaction with an antibody raised against an α-amylase having one of the amino acid sequences shown in SEQ ID No. 1, SEQ ID No. 2, SEQ ID No. 3 and SEQ ID No. 7, respectively, and/or b) that the α-amylase is encoded by a DNA sequence which hybridizes with the same probe as a DNA sequence encoding an α-amylase having one of the amino acid sequences shown in SEQ ID No. 1, SEQ ID No. 2, SEQ ID No. 3 and SEQ ID No. 7, respectively.

As already mentioned, with regard to determination of the degree of homology of polypeptides (such as enzymes), amino acid sequence comparisons can be performed using known algorithms, such as the one described by Lipman and Pearson (1985).

Assays for immunological cross-reactivity may be carried out using an antibody raised against, or reactive with, at least one epitope of the α-amylase having the amino acid sequence shown in SEQ ID No. 1, or of the α-amylase having the amino acid sequence shown in SEQ ID No. 2, or of the α-amylase having the amino acid sequence shown in SEQ ID No. 3, or of the α-amylase having the amino acid sequence shown in SEQ ID No. 7.

The antibody, which may either be monoclonal or polyclonal, may be produced by methods known in the art, e.g. as described by Hudson et al. (1989). Examples of suitable assay techniques well known in the art include Western Blotting and Radial Immunodiffusion Assay, e.g. as described by Hudson et al. (1989).

The oligonucleotide probe for use in the identification of suitable parent α-amylases on the basis of probe hybridization [criterion b) above] may, by way of example, suitably be prepared on the basis of the full or partial amino acid sequence of an α-amylase having one of the sequences shown in SEQ ID No. 1, SEQ ID No. 2, SEQ ID No. 3 and SEQ ID No. 7, respectively, or on the basis of the full or partial nucleotide sequence corresponding thereto.

Suitable conditions for testing hybridization involve presoaking in 5×SSC and prehybridizing for 1 h at ~40° C. in a solution of 20% formamide, 5×Denhardt's solution, 50 mM sodium phosphate, pH 6.8, and 50 μg of denatured sonicated calf thymus DNA, followed by hybridization in the same solution supplemented with 100 μM ATP for 18 h at ~40° C., or using other methods described by, e.g., Sambrook et al. (1989).

Influence of Mutations on Particular Properties

From the results obtained by the present inventors it appears that changes in a particular property, e.g. thermal stability or oxidation stability, exhibited by a variant relative to the parent α-amylase in question can to a considerable extent be correlated with the type of, and positioning of, mutation(s) (amino acid substitutions, deletions or insertions) in the variant. It is to be understood, however, that the observation that a particular mutation or pattern of mutations leads to changes in a given property in no way excludes the possibility that the mutation(s) in question can also influence other properties.

Oxidation stability: With respect to increasing the oxidation stability of an α-amylase variant relative to its parent α-amylase, it appears to be particularly desirable that at least one, and preferably multiple, oxidizable amino acid residue (s) of the parent has/have been deleted or replaced (i.e. substituted by) a different amino acid residue which is less susceptible to oxidation than the original oxidizable amino acid residue.

Particularly relevant oxidizable amino acid residues in this connection are cysteine, methionine, tryptophan and tyrosine. Thus, for example, in the case of parent α-amylases containing cysteine it is anticipated that deletion of cysteine residues, or substitution thereof by less oxidizable amino acid residues, will be of importance in obtaining variants with improved oxidation stability relative to the parent α-amylase.

In the case of the above-mentioned parent α-amylases having the amino acid sequences shown in SEQ ID No. 1, SEQ ID No. 2 and SEQ ID No. 7, respectively, all of which contain no cysteine residues but have a significant methionine content, the deletion or substitution of methionine residues is particularly relevant with respect to achieving improved oxidation stability of the resulting variants. Thus, deletion or substitution [e.g. by threonine (T), or by one of the other amino acids listed above] of one or more of the methionine residues in positions M9, M10, M105, M202, M208, M261, M309, M382, M430 and M440 of the amino acid sequences shown in SEQ ID No. 1, SEQ ID No. 2 and SEQ ID No. 7, and/or in position M323 of the amino acid sequence shown in SEQ ID No. 2 (or deletion or substitution of methionine residues in equivalent positions in the sequence of another α-amylase meeting one of the other criteria for a parent α-amylase mentioned above) appear to be particularly effective with respect to increasing the oxidation stability.

In the case of the parent α-amylase having the amino acid sequence shown in SEQ ID No. 3, relevant amino acid residues which may be deleted or substituted with a view to improving the oxidation stability include the single cysteine residue (C363) and—by analogy with the sequences shown in SEQ ID No. 1 and SEQ ID No. 3—the methionine residues located in positions M8, M9, M96, M200, M206, M284, M307, M311, M316 and M438.

In this connection, the term "equivalent position" denotes a position which, on the basis of an alignment of the amino acid sequence of the parent α-amylase in question with the "reference" α-amylase amino acid sequence in question (for example the sequence shown in SEQ ID No. 1) so as to achieve juxtapositioning of amino acid residues/regions which are common to both, corresponds most closely to (e.g. is occupied by the same amino acid residue as) a particular position in the reference sequence in question.

Particularly interesting mutations in connection with modification (improvement) of the oxidation stability of the α-amylases having the amino acid sequences shown in SEQ ID No. 1, SEQ ID No. 2 and SEQ ID No. 7, respectively, are one or more of the following methionine substitutions (or equivalents thereof in the amino acid sequences of other α-amylases meeting the requirements of a parent α-amylase in the context of the invention): M202A,R,N,D,Q,E,G,H,I, L,K,F,P,S,T,W,Y,V.

Further relevant methionine substitutions in the amino acid sequence shown in SEQ ID No. 2 are: M323A,R,N,D, Q,E,G,H,I,L,K,F,P,S,T,W,Y,V.

Particularly interesting mutations in connection with modification (improvement) of the oxidation stability of the α-amylase having the amino acid sequence shown in SEQ ID No. 3 are one or more of the following methionine substitutions:

M200A,R,N,D,Q,E,G,H,I,L,K,F,P,S,T,W,Y,V;
M311A,R,N,D,Q,E,G,H,I,L,K,F,P,S,T,W,Y,V; and
M316A,R,N,D,Q,E,G,H,I,L,K,F,P,S,T,W,Y,V.

Thermal stability: With respect to increasing the thermal stability of an α-amylase variant relative to its parent α-amylase, it appears to be particularly desirable to delete at least one, and preferably two or even three, of the following amino acid residues in the amino acid sequence shown in SEQ ID No. 1 (or their equivalents): F180, R181, G182, T183, G184 and K185. The corresponding, particularly relevant (and equivalent) amino acid residues in the amino acid sequences shown in SEQ ID No. 2, SEQ ID No. 3 and SEQ ID No. 7, respectively, are: F180, R181, G182, D183, G184 and K185 (SEQ ID No. 2); F178, R179, G180, I 181, G182 and K183 (SEQ ID No. 3); and F180, R181, G182, H183, G184 and K185 (SEQ ID No. 7).

Particularly interesting pairwise deletions of this type are as follows:

R181*+G182*; and T183*+G184* (SEQ ID No. 1);
R181*+G182*; and D183*+G184* (SEQ ID No. 2);
R179*+G180*; and I181*+G182* (SEQ ID No. 3); and
R181*+G182*; and H183*+G184* (SEQ ID No. 7)

(or equivalents of these pairwise deletions in another α-amylase meeting the requirements of a parent α-amylase in the context of the present invention).

Other mutations which appear to be of importance in connection with thermal stability are substitutions of one or more of the amino acid residues from P260 to I275 in the sequence shown in SEQ ID No. 1 (or equivalents thereof in another parent α-amylase in the context of the invention), such as substitution of the lysine residue in position 269.

Examples of specific mutations which appear to be of importance in connection with the thermal stability of an α-amylase variant relative to the parent α-amylase in question are one or more of the following substitutions in the amino acid sequence shown in SEQ ID No. 1 (or equivalents thereof in another parent α-amylase in the context of the invention): K269R; P260E, R124P, M105F,I,L,V; M208F, W,Y; L217I; V206I,L,F.

For the parent α-amylase having the amino acid sequence shown in SEQ ID No. 2, important further (equivalent) mutations are, correspondingly, one or more of the substitutions: M105F,I,L,V; M208F,W,Y; L217I; V206I,L,F; and K269R.

For the parent α-amylase having the amino acid sequence shown in SEQ ID No. 3, important further (equivalent) mutations are, correspondingly, one or both of the substitutions: M206F,W,Y; and L215I.

For the parent α-amylase having the amino acid sequence shown in SEQ ID No. 7. important further (equivalent) mutations are, correspondingly, one or more of the substitutions: M105F,I,L,V; M208F,W,Y; L217I; and K269R.

Still further examples of mutations which appear to be of importance, inter alia, in achieving improved thermal stability of an α-amylase variant relative to the parent α-amylase in question are one or more of the following substitutions in the amino acid sequences shown in SEQ ID No. 1, SEQ ID No. 2 and SEQ ID No. 7 (or equivalents thereof in another parent α-amylase in the context of the invention): A354C+V479C; L351C+M430C; N457D,E+ K385R; L355D,E+M430R,K; L355D,E+I411R,K; and N457D,E.

$Ca^{2+}$ dependency: With respect to achieving decreased $Ca^{2+}$ dependency of an α-amylase variant relative to its parent α-amylase [i.e. with respect to obtaining a variant which exhibits satisfactory amylolytic activity in the presence of a lower concentration of calcium ion in the extraneous medium than is necessary for the parent enzyme, and which, for example, therefore is less sensitive than the parent to calcium ion-depleting conditions such as those obtaining in media containing calcium-complexing agents (such as certain detergent builders)], it appears to be particularly desirable to incorporate one or more of the following substitutions in the amino acid sequences shown in SEQ ID No. 1, SEQ ID No. 2 and SEQ ID No. 7 (or an equivalent substitution in another parent α-amylase in the context of the invention): Y243F, K108R, K179R, K239R, K242R, K269R, D163N, D188N, D192N, D199N, D205N, D207N, D209N, E190Q, E194Q and N106D.

In the case of the amino acid sequence shown in SEQ ID No. 3, particularly desirable substitutions appear, correspondingly (equivalently), to be one or more of the following: K107R, K177R, K237R, K240R, D162N, D186N, D190N, D197N, D203N, D205N, D207N, E188Q and E192Q.

As well as the above-mentioned replacements of D residues with N residues, or of E residues with Q residues, other relevant substitutions in the context of reducing $Ca^{2+}$ dependency are replacement of the D and/or E residues in question with any other amino acid residue.

Further substitutions which appear to be of importance in the context of achieving reduced $Ca^{2+}$ dependency are pairwise substitutions of the amino acid residues present at: positions 113 and 151, and positions 351 and 430, in the amino acid sequences shown in SEQ ID No. 1, SEQ ID No. 2 and SEQ ID No. 7; and at: positions 112 and 150, and positions 349 and 428, in the amino acid sequence shown in SEQ ID No. 3 (or equivalent pairwise substitutions in another parent α-amylase in the context of the invention), i.e. pairwise substitutions of the following amino acid residues:

G113+N151 (in relation to SEQ ID No.1); A113+T151 (in relation to SEQ ID No. 2 and SEQ ID No. 7); and G112+T150 (in relation to SEQ ID No. 3); and L351+M430 (in relation to SEQ ID No.1, SEQ ID No. 2 and SEQ ID No. 7); and L349+I428 (in relation to SEQ ID No. 3).

Particularly interesting pairwise substitutions of this type with respect to achieving decreased $Ca^{2+}$ dependency are the following:

G113T+N151I (in relation to SEQ ID No.1); A113T+T151I (in relation to SEQ ID No. 2 and SEQ ID No. 7); and G112T+T150I (in relation to SEQ ID No. 3); and L351C+M430C (in relation to SEQ ID No. 1, SEQ ID No. 2 and SEQ ID No. 7); and L349C+I428C (in relation to SEQ ID No. 3).

In connection with substitutions of relevance for $Ca^{2+}$ dependency, some other substitutions which appear to be of importance in stabilizing the enzyme conformation, and which it is contemplated may achieve this by, e.g., enhancing the strength of binding or retention of calcium ion at or within a calcium binding site within the α-amylolytic enzyme, are one or more of the following substitutions in the amino acid sequences shown in SEQ ID No. 1, SEQ ID No. 2 and SEQ ID No. 7 (or an equivalent substitution in another parent α-amylase in the context of the invention): G304W,F,Y,R,I,L,V,Q,N; G305A,S,N,D,Q,E,R,K; and H408Q,E.

Corresponding (equivalent) substitutions in the amino acid sequence shown in SEQ ID No. 3 are: G302W,F,Y,R,I,L,V,Q,N; and G303A,S,N,D,Q,E,R,K.

Further mutations which appear to be of importance in the context of achieving reduced $Ca^{2+}$ dependency are pairwise deletions of amino acids (i.e. deletion of two amino acids) at positions selected among R181, G182, T183 and G184 in the amino acid sequence shown in SEQ ID No.1 (or equivalent positions in the amino acid sequence of another α-amylase meeting the requirements of a parent α-amylase in the context of the invention). Such pairwise deletions are thus the following:

R181*+G182*; T183*+G184*; R181*+T183*; G182*+T183*; G182*+G184*; and R181*+G184* (SEQ ID No. 1);

R181*+G182*; D183*+G184*; R181*+D183*; G182*+D183*; G182*+G184*; and R181*+G184*(SEQ ID No. 2);

R179*+G180*; I181*+G182*; R179*+I181*; G180*+I181*; G180*+G182*; and R179*+G182*(SEQ ID No. 3); and R181*+G182*; H183*+G184*; R181*+H183*; G182*+H183*; G182*+G184*; and R181*+G184*(SEQ ID No. 7);

(or equivalents of these pairwise deletions in another α-amylase meeting the requirements of a parent α-amylase in the context of the present invention).

Isoelectric point (pI): Preliminary results indicate that the washing performance, e.g. the laundry washing performance, of an α-amylase is optimal when the pH of the washing liquor (washing medium) is close to the pI value for the α-amylase in question. It will thus be desirable, where appropriate, to produce an α-amylase variant having an isoelectric point (pI value) which is better matched to the pH of a medium (such as a washing medium) in which the enzyme is to be employed than the isoelectric point of the parent α-amylase in question.

With respect to decreasing the isoelectric point, preferred mutations in the amino acid sequence shown in SEQ ID No. 1 include one or more of the following substitutions: Q86E, R124P, S154D), T183D, V222E, P260E, R310A, Q346E, Q391E, N437E, K444Q and R452H. Appropriate combinations of these substitutions in the context of decreasing the isoelectric point include: Q391E+K444Q; and Q391E+K444Q+S154D.

Correspondingly, preferred mutations in the amino acid sequence shown in SEQ ID No. 3 with respect to decreasing the isoelectric point include one or more of the substitutions: L85E, S153D, I181D, K220E, P258E, R308A, P344E, Q358E and S435E.

With respect to increasing the isoelectric point, preferred mutations in the amino acid sequence shown in SEQ ID No. 2 include one or more of the following substitutions: E86Q, L; D154S; D183T,I; E222V,K; E260P; A310R; E346Q,P; E437N,S; and H452R.

In the Experimental section below, the construction of a number of variants according to the invention is described.

α-Amylase variants of the invention will, apart from having one or more improved properties as discussed above, preferably be such that they have a higher starch hydrolysis velocity at low substrate concentrations than the parent α-amylase. Alternatively, an α-amylase variant of the invention will preferably be one which has a higher $V_{max}$ and/or a lower $K_m$ than the parent α-amylase when tested under the same conditions. In the case of a hybrid α-amylase, the "parent α-amylase" to be used for the comparison should be the one of the constituent enzymes having the best performance.

$V_{max}$ and $K_m$ (parameters of the Michaelis-Menten equation) may be determined by well-known procedures.

Methods of Preparing α-amylase Variants

Several methods for introducing mutations into genes are known in the art. After a brief discussion of the cloning of α-amylase-encoding DNA sequences, methods for generating mutations at specific sites within the α-amylase-encoding sequence will be discussed.

Cloning a DNA Sequence Encoding an α-amylase

The DNA sequence encoding a parent α-amylase may be isolated from any cell or microorganism producing the α-amylase in question, using various methods well known in the art. First, a genomic DNA and/or cDNA library should be constructed using chromosomal DNA or messenger RNA from the organism that produces the α-amylase to be studied. Then, if the amino acid sequence of the α-amylase is known, homologous, labelled oligonucleotide probes may be synthesized and used to identify α-amylase-encoding clones from a genomic library prepared from the organism in question. Alternatively, a labelled oligonucleotide probe containing sequences homologous to a known α-amylase gene could be used as a probe to identify α-amylase-encoding clones, using hybridization and washing conditions of lower stringency.

Yet another method for identifying α-amylase-encoding clones would involve inserting fragments of genomic DNA into an expression vector, such as a plasmid, transforming α-amylase-negative bacteria with the resulting genomic DNA library, and then plating the transformed bacteria onto agar containing a substrate for α-amylase, thereby allowing clones expressing the α-amylase to be identified.

Alternatively, the DNA sequence encoding the enzyme may be prepared synthetically by established standard methods, e.g. the phosphoamidite method described by S. L. Beaucage and M. H. Caruthers (1981) or the method described by Matthes et al. (1984). In the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

Site-directed Mutagenesis

Once an α-amylase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the α-amylase-encoding sequence, is created in a vector carrying the α-amylase gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into α-amylase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

Random mutagenesis is suitably performed either as localized or region-specific random mutagenesis in at least three parts of the gene translating to the amino acid sequence shown in question, or within the whole gene.

For region-specific random mutagenesis with a view to improving the thermal stability, the following codon positions, in particular, may appropriately be targeted (using one-letter amino acid abbreviations and the numbering of the amino acid residues in the sequence in question):

In the amino acid sequence shown in SEQ ID No. 1:
  120-140=VEVNRSNRNQETSGEYAIEAW
  178-187=YKFRGTGKAW
  264-277=VAEFWKNDLGAIEN
In the amino acid sequence shown in SEQ ID No. 2:
  120-140=VEVNPNNRNQEISGDYTIEAW
  178-187=YKFRGDGKAW
  264-277=VAEFWKNDLGALEN
In the amino acid sequence shown in SEQ ID No. 3:
  119-139=VEVNPSDRNQEISGTYQIQAW
  176-185=YKFRGIGKAW
  262-275=VGEYWSYDINKLHN
In the amino acid sequence shown in SEQ ID No. 7:
  120-140=VEVNPNNRNQEVTGEYTIEAW
  178-187=YKFRGHGKAW
  264-277=VAEFWKNDLGAIEN With a view to achieving reduced $Ca^{2+}$ dependency, the following codon positions, in particular, may appropriately be targeted:

In the amino acid sequence shown in SEQ ID No. 1:
  178-209=
    YKFRGTGKAWDWEVDTENGNYDYLMYAD-VDMD
  237-246=AVKHIKYSFT
In the amino acid sequence shown in SEQ ID No. 2:
  178-209=
    YKFRGDGKAWDWEVDSENGNYDYLMYAD-VDMD
  237-246=AVKHIKYSFT
In the amino acid sequence shown in SEQ ID No. 7:
  178-209=
    YKFRGHGKAWDWEVDTENGNYDYLMYA-DIDMD
  237-246=AVKHIKYSFT With a view to achieving improved binding of a substrate (i.e. improved binding of a carbohydrate species—such as amylose or amylopectin—which is a substrate for α-amylolytic enzymes) by an α-amylase variant, modified (e.g. higher) substrate specificity and/or modified (e.g. higher) specificity with respect to cleavage (hydrolysis) of substrate, it appears that the following codon positions for the amino acid sequence shown in SEQ ID No. 1 (or equivalent codon positions for another parent α-amylase in the context of the invention) may particularly appropriately be targeted:

In the amino acid sequence shown in SEQ ID No. 1:
  15-20 WYLPND
  52-58=SQNDVGY
  72-78=KGTVRTK
  104-111=VMNHKGGA
  165-174=TDWDQSRQLQ
  194-204=ENGNYDYLMYA
  234-240=RIDAVKH
  332-340=HDSQPGEAL The random mutagenesis of a DNA sequence encoding a parent α-amylase to be performed in accordance with step a) of the above-described method of the invention may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed.

The doping or spiking may be done so that codons for unwanted amino acids are avoided. The doped or spiked oligonucleotide can be incorporated into the DNA encoding the amylolytic enzyme by any published technique, using e.g. PCR, LCR or any DNA polymerase and ligase.

When PCR-generated mutagenesis is used, either a chemically treated or non-treated gene encoding a parent α-amylase enzyme is subjected to PCR under conditions that increase the misincorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the amylolytic enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or cDNA library prepared from an organism expressing the parent amylolytic enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step (b) or the screening step (c) being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram negative bacteria such as *E. coli*.

The mutated DNA sequence may further comprise a DNA sequence encoding functions permitting expression of the mutated DNA sequence.

Localized random mutagenesis: the random mutagenesis may advantageously be localized to a part of the parent α-amylase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently performed by use of a filter assay based on the following principle:

A microorganism capable of expressing the mutated amylolytic enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, flourescence, precipitation, pH indicator, IR-absorbance or any other known technique for detection of enzymatic activity.

The detecting compound may be immobilized by any immobilizing agent e.g. agarose, agar, gelatine, polyacrylamide, starch, filter paper, cloth; or any combination of immobilizing agents.

α-Amylase activity is detected by Cibacron Red labelled amylopectin, which is immobilized on agarose. For screening for variants with increased thermal and high-pH stability, the filter with bound α-amylase variants is incubated in a buffer at pH 10.5 and 60° or 65° C. for a specified time, rinsed briefly in deionized water and placed on the amylopectin-agarose matrix for activity detection. Residual activity is seen as lysis of Cibacron Red by amylopectin degradation. The conditions are chosen to be such that activity due to the α-amylase having the amino acid sequence shown in SEQ ID No.1 can barely be detected. Stabilized variants show, under the same conditions, increased color intensity due to increased liberation of Cibacron Red.

For screening for variants with an activity optimum at a lower temperature and/or over a broader temperature range, the filter with bound variants is placed directly on the amylopectin-Cibacron Red substrate plate and incubated at the desired temperature (e.g. 4° C., 10° C. or 30° C.) for a specified time. After this time activity due to the α-amylase having the amino acid sequence shown in SEQ ID No.1 can barely be detected, whereas variants with optimum activity at a lower temperature will show increase amylopectin lysis. Prior to incubation onto the amylopectin matrix, incubation in all kinds of desired media—e.g. solutions containing $Ca^{2+}$, detergents, EDTA or other relevant additives—can be carried out in order to screen for changed dependency or for reaction of the variants in question with such additives.

Methods of Preparing Hybrid α-amylases

As an alternative to site-specific mutagenesis, α-amylase variants which are hybrids of at least two constituent α-amylases may be prepared by combining the relevant parts of the respective genes in question.

Naturally occurring enzymes may be genetically modified by random or site directed mutagenesis as described above. Alternatively, part of one enzyme may be replaced by a part of another to obtain a chimeric enzyme. This replacement can be achieved either by conventional in vitro gene splicing techniques or by in vivo recombination or by combinations of both techniques. When using conventional in vitro gene splicing techniques, a desired portion of the α-amylase gene coding sequence may be deleted using appropriate site-specific restriction enzymes; the deleted portion of the coding sequence may then be replaced by the insertion of a desired portion of a different α-amylase coding sequence so that a chimeric nucleotide sequence encoding a new α-amylase is produced. Alternatively, α-amylase genes may be fused, e.g. by use of the PCR overlay extension method described by Higuchi et al. 1988.

The in vivo recombination techniques depend on the fact that different DNA segments with highly homologous regions (identity of DNA sequence) may recombine, i.e. break and exchange DNA, and establish new bonds in the homologous regions. Accordingly, when the coding sequences for two different but homologous amylase enzymes are used to transform a host cell. recombination of homologous sequences in vivo will result in the production of chimeric gene sequences. Translation of these coding sequences by the host cell will result in production of a chimeric amylase gene product. Specific in vivo recombination techniques are described in U.S. Pat. No. 5,093,257 and EP 252 666.

Alternatively, the hybrid enzyme may be synthesized by standard chemical methods known in the art. For example, see Hunkapiller et al. (1984). Accordingly, peptides having the appropriate amino acid sequences may be synthesized in whole or in part and joined to form hybrid enzymes (variants) of the invention.

Expression of α-amylase Variants

According to the invention, a mutated α-amylase-encoding DNA sequence produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding an α-amylase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding an α-amylase variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus Amyloliquefaciens* α-amylase (amyQ), the promoters of the *Bacillus subtilis* xy1A and xy1B genes etc. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB 110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular.

Procedures suitable for constructing vectors of the invention encoding an α-amylase variant, and containing the promoter, terminator and other elements, respectively, are well known to persons skilled in the art [cf., for instance, Sambrook et al. (1989)].

The cell of the invention, either comprising a DNA construct or an expression vector of the invention as defined above, is advantageously used as a host cell in the recombinant production of an α-amylase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulars, Bacillus lautus, Bacillus megaterium, Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

The yeast organism may favorably be selected from a species of Saccharomyces or Schizosaccharomyces, e.g. *Saccharomyces cerevisiae*. The filamentous fungus may advantageously belong to a species of Aspergillus, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing an α-amylase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant of the invention. Suitable media are available from commercial suppliers or may be prepared according to published recipes (e.g. as described in catalogues of the American Type Culture Collection).

The α-amylase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

Owing to their activity at alkaline pH values, α-amylase variants of the invention are well suited for use in a variety of industrial processes. In particular, they find potential applications as a component in washing, dishwashing and hard surface cleaning detergent compositions (vide infra), but may also be useful in the production of sweeteners and ethanol from starch. Conditions for conventional starch-converting processes and liquefaction and/or saccharification processes are described in, for instance, U.S. Pat. No. 3,912,590, EP 252,730 and EP 63,909.

Some areas of application of α-amylase variants of the invention are outlined below.

Paper-related applications: α-Amylase variants of the invention possess properties of value in the production of lignocellulosic materials, such as pulp, paper and cardboard, from starch-reinforced waste paper and waste cardboard, especially where repulping occurs at a pH above 7, and where amylases can facilitate the disintegration of the waste material through degradation of the reinforcing starch.

α-Amylase variants of the invention are well suited for use in the deinking/recycling processes of making paper out of starch-coated or starch-containing waste printed paper. It is usually desirable to remove the printing ink in order to produce new paper of high brightness; examples of how the variants of the invention may be used in this way are described in PCT/DK94/00437.

α-Amylase variants of the invention may also be very useful in modifying starch where enzymatically modified starch is used in papermaking together with alkaline fillers such as calcium carbonate, kaolin and clays. With alkaline α-amylase variants of the invention it is feasible to modify the starch in the presence of the filler, thus allowing for a simpler, integrated process.

Textile desizing: α-Amylase variants of the invention are also well suited for use in textile desizing. In the textile processing industry, α-amylases are traditionally used as auxiliaries in the desizing process to facilitate the removal of starch-containing size which has served as a protective coating on weft yarns during weaving.

Complete removal of the size coating after weaving is important to ensure optimum results in subsequent processes in which the fabric is scoured, bleached and dyed. Enzymatic starch degradation is preferred because it does not harm the fibers of the textile or fabric.

In order to reduce processing costs and increase mill throughput, the desizing processing is sometimes combined with the scouring and bleaching steps. In such cases, non-enzymatic auxiliaries such as alkali or oxidation agents are typically used to break down the starch, because traditional α-amylases are not very compatible with high pH levels and bleaching agents. The non-enzymatic breakdown of the starch size does lead to some fibre damage because of the rather aggressive chemicals used.

α-Amylase variants of the invention exhibiting improved starch-degrading performance at relatively high pH levels and in the presence of oxidizing (bleaching) agents are thus well suited for use in desizing processes as described above, in particular for replacement of non-enzymatic desizing agents currently used. The α-amylase variant may be used alone, or in combination with a cellulase when desizing cellulose-containing fabric or textile.

Beer production: α-Amylase variants of the invention are also believed to be very useful in beer-making processes; in such processes the variants will typically be added during the mashing process.

Applications in detergent additives and detergent compositions for washing or dishwashing: Owing to the improved washing and/or dishwashing performance which will often be a consequence of improvements in properties as discussed above, numerous α-amylase variants (including hybrids) of the invention are particularly well suited for incorporation into detergent compositions, e.g. detergent compositions intended for performance in the pH range of 7–13, particularly the pH range of 8–11. According to the invention, the α-amylase variant may be added as a component of a detergent composition. As such, it may be included in the detergent composition in the form of a detergent additive.

Thus, a further aspect of the invention relates to a detergent additive comprising an α-amylase variant according to the invention. The enzymes may be included in a detergent composition by adding separate additives containing one or more enzymes, or by adding a combined additive comprising all of these enzymes. A detergent additive of the invention. i.e. a separated additive or a combined additive, can be formulated, e.g., as a granulate, liquid, slurry, etc. Preferred enzyme formulations for detergent additives are granulates (in particular non-dusting granulates), liquids (in particular stabilized liquids), slurries or protected enzymes (vide infra).

The detergent composition as well as the detergent additive may additionally comprise one or more other enzymes conventionally used in detergents, such as proteases, lipases, amylolytic enzymes, oxidases (including peroxidases), or cellulases.

It has been found that substantial improvements in washing and/or dishwashing performance may be obtained when α-amylase is combined with another amylolytic enzyme, such as a pullulanase, an iso-amylase, a beta-amylase, an amyloglucosidase or a CGTase. Examples of commercially available amylolytic enzymes suitable for the given purpose are AMG™, Novamyl™ and Promozyme™, all of which available from Novo Nordisk A/S, Bagsvaerd, Denmark. Accordingly, a particular embodiment of the invention relates to a detergent additive comprising an α-amylase variant of the invention in combination with at least one other amylolytic enzyme (e.g. chosen amongst those mentioned above).

Non-dusting granulates may be produced, e.g., as disclosed in U.S. Pat. No. 4,106,991 and U.S. Pat. No. 4,661,452, and may optionally be coated by methods known in the art; further details concerning coatings are given below. When a combination of different detergent enzymes is to be employed, the enzymes may be mixed before or after granulation.

Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238 216.

As already indicated, a still further aspect of the invention relates to a detergent composition, e.g. for laundry washing, for dishwashing or for hard-surface cleaning, comprising an α-amylase variant (including hybrid) of the invention, and a surfactant.

The detergent composition of the invention may be in any convenient form, e.g. as powder, granules or liquid. A liquid detergent may be aqueous, typically containing up to 90% of water and 0–20% of organic solvent, or non-aqueous, e.g. as described in EP Patent 120,659.

Detergent Compositions

When an α-amylase variant of the invention is employed as a component of a detergent composition (e.g. a laundry washing detergent composition, or a dishwashing detergent composition), it may, for example, be included in the detergent composition in the form of a non-dusting granulate, a stabilized liquid, or a protected enzyme. As mentioned above, non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Enzymes added in the form of liquid enzyme preparations may, as indicated above, be stabilized by, e.g., the addition of a polyol such as propylene glycol, a sugar or sugar alcohol, lactic acid or boric acid according to established methods. Other enzyme stabilizers are well known in the art.

Protected enzymes for inclusion in a detergent composition of the invention may be prepared, as mentioned above, according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or amphoteric (zwitterionic). The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), alcohol propoxylate, carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as pullulanase, esterase, lipase, cutinase, protease, cellulase, peroxidase, or oxidase, e.g., laccase.

Normally the detergent contains 1–65% of a detergent builder (although some dishwashing detergents may contain even up to 90% of a detergent builder) or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst).

The detergent builders may be subdivided into phosphorus-containing and non-phosphorous-containing types. Examples of phosphorus-containing inorganic alkaline detergent builders include the water-soluble salts, especially alkali metal pyrophosphates, orthophosphates, polyphosphates and phosphonates. Examples of non-phosphorus-containing inorganic builders include water-soluble alkali metal carbonates, borates and silicates, as well as layered disilicates and the various types of water-insoluble crystalline or amorphous alumino silicates of which zeolites are the best known representatives.

Examples of suitable organic builders include alkali metal, ammonium or substituted ammonium salts of succinates, malonates, fatty acid malonates, fatty acid sulphonates. carboxymethoxy succinates, polyacetates, carboxylates, polycarboxylates, aminopolycarboxylates and polyacetyl carboxylates.

The detergent may also be unbuilt, i.e. essentially free of detergent builder.

The detergent may comprise one or more polymers. Examples are carboxymethylcellulose (CMC; typically in the form of the sodium salt), poly(vinylpyrrolidone) (PVP), polyethyleneglycol (PEG), poly(vinyl alcohol) (PVA), polycarboxylates such as polyacrylates, polymaleates, maleic/acrylic acid copolymers and lauryl methacrylate/acrylic acid copolymers.

The detergent composition may contain bleaching agents of the chlorine/bromine-type or the oxygen-type. The bleaching agents may be coated or encapsulated. Examples of inorganic chlorine/bromine-type bleaches are lithium, sodium or calcium hypochlorite or hypobromite as well as chlorinated trisodium phosphate. The bleaching system may also comprise a $H_2O_2$ source such as perborate or percarbonate which may be combined with a peracid-forming bleach activator such as tetraacetylethylenediamine (TAED) or nonanoyloxybenzenesulfonate (NOBS).

Examples of organic chlorine/bromine-type bleaches are heterocyclic N-bromo and N-chloro imides such as trichloroisocyanuric, tribromoisocyanuric, dibromoisocyanuric and dichloroisocyanuric acids, and salts thereof with water solubilizing cations such as potassium and sodium. Hydantoin compounds are also suitable. The bleaching system may also comprise peroxyacids of, e.g., the amide, imide, or sulfone type.

In dishwashing detergents the oxygen bleaches are preferred, for example in the form of an inorganic persalt, preferably with a bleach precursor or as a peroxy acid compound. Typical examples of suitable peroxy bleach compounds are alkali metal perborates, both tetrahydrates and monohydrates, alkali metal percarbonates, persilicates and perphosphates. Preferred activator materials are TAED or NOBS.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708. The enzymes of the invention may also be stabilized by adding reversible enzyme inhibitors, e.g., of the protein type (as described in EP 0 544 777 B1) or the boronic acid type.

The detergent may also contain other conventional detergent ingredients such as, e.g., fabric conditioners including clays, deflocculant material, foam boosters/foam depressors (in dishwashing detergents foam depressors), suds suppressors, anti-corrosion agents, soil-suspending agents, anti-soil-redeposition agents, dyes, dehydrating agents, bactericides, optical brighteners, or perfume.

The pH (measured in aqueous solution at use concentration) will usually be neutral or alkaline, e.g. in the range of 7–11.

Particular forms of laundry detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g. $C_{12-18}$ alcohol, 1–2 EO) or alkyl sulfate (e.g. $C_{16-18}$) | 1–4% |
| Alcohol ethoxylate (e.g. $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g. $C_{12-18}$ alcohol, 1–2 EO) or alkyl sulfate (e.g. $C_{16-18}$) | 1–3% |
| Alcohol ethoxylate (e.g. $C_{14-15}$ alcohol, 7 EO) | 5–9% |
| Sodium carbonate (as $Na_2CO_3$) | 15–21% |
| Soluble silicate (as $Na_2O, 2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g. maleic/acrylic acid copolymer, PVP, PEG) | 1–6% |
| Enzymes (calculated as pure enzyme protein) | 0.0001–0.1% |
| Minor ingredients (e.g. suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g. $C_{12-15}$ alcohol, 7 EO) | 7–14% |
| Soap as fatty acid (e.g. $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g. EDTMPA) | 0–1% |
| Carboxymethylcellulose | 0–2% |
| Polymers (e.g. maleic/acrylic acid copolymer, PVP, PEG) | 0–3% |
| Enzymes (calculated as pure enzyme protein) | 0.0001–0.1% |
| Minor ingredients (e.g. suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g. $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g. maleic/acrylic acid copolymer, PVP, PEG) | 1–3% |
| Enzymes (calculated as pure enzyme protein) | 0.0001–0.1% |
| Minor ingredients (e.g. suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO or $C_{12-15}$ alcohol, 5 EO) | 12–18% |
| Soap as fatty acid (e.g. oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g. PVP, PEG) | 0–3% |
| Borate (as $B_4O_7^{2-}$) | 0–2% |
| Ethanol | 0–3% |
| Propylene glycol | 8–14% |
| Enzymes (calculated as pure enzyme protein) | 0.0001–0.1% |
| Minor ingredients (e.g. disperants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g. $C_{12-15}$ alcohol, 7 EO, or $C_{12-15}$ alcohol, 5 EO) | 3–9% |
| Soap as fatty acid (e.g. oleic acid) | 3–10% |
| Zeolite (as $NaAlSiO_4$) | 14–22% |
| Potassium citrate | 9–18% |
| Borate (as $B_4O_7^{2-}$) | 0–2% |
| Carboxymethylcellulose | 0–2% |
| Polymers (e.g. PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g. dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g. maleic/acrylic acid copolymer, PEG) | 1–5% |
| Enzymes (calculated as pure enzyme protein) | 0.0001–0.1% |
| Minor ingredients (e.g. optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g. PVP, maleic/acrylic acid copolymer, PEG) | 1–5% |
| Enzymes (calculated as pure enzyme protein) | 0.0001–0.1% |
| Minor ingredients (e.g. suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g. NOBS or TAED) | 1–5% |
| Carboxymethylcellulose | 0–2% |
| Polymers (e.g. polycarboxylate or PEG) | 1–5% |
| Enzymes (calculated as pure enzyme protein) | 0.0001–0.1% |
| Minor ingredients (e.g. optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g. $C_{12-15}$ alcohol, 2–3 EO) | 8–15% |
| Alcohol ethoxylate (e.g. $C_{12-15}$ alcohol, 7 EO, $C_{12-15}$ alcohol, 5 EO) | 3–9% |
| Soap as fatty acid (e.g. lauric acid) | 0–3% |
| Aminoethanol | 1–5% |
| Sodium citrate | 5–10% |
| Hydrotrope (e.g. sodium toluene sulfonate) | 2–6% |
| Borate (as $B_4O_7^{2-}$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g. polymers, disperants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g. $C12_{-15}$ alcohol, 7 EO, or $C_{12-15}$ alcohol, 5 EO) | 6–12% |
| Aminoethanol | 2–6% |
| Citric acid | 8–14% |
| Borate (as $B_4O_7^{2-}$) | 1–3% |
| Polymer (e.g. maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g. hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g. alcohol ethoxylate) | 1–10% |
| Sodium carbonate (as $Na_2CO_3$) | 8–25% |
| Soluble silicates (as $Na_2O, 2SiO_2$) | 5–15% |
| Sodium sulfate (as $Na_2SO_4$) | 0–5% |
| Zeolite (as $NaAlSiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g. perfume, optical brighteners) | 0–3% |

13) Detergent formulations as described in 1)–12) wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaAlSiO_4$) | 10–20% |
| Layered disilicate (e.g. SK56 from Hoechst) | 10–20% |
| Sodium carbonate (as $Na_2CO_3$) | 3–12% |
| Soluble silicate (as $Na_2O, 2SiO_2$) | 0–6% |
| Sodium citrate | 4–8% |
| Sodium percarbonate | 13–22% |
| TAED | 3–8% |
| Polymers (e.g. polycarboxylates and PVP) | 0–5% |
| Enzymes (calculated as pure enzyme protein) | 0.0001–0.1% |
| Minor ingredients (e.g. optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |
| Soap | 1–4% |
| Zeolite MAP or zeolite A | 35–45% |
| Sodium carbonate (as $Na_2CO_3$) | 2–8% |
| Soluble silicate (as $Na_2O, 2SiO_2$) | 0–4% |
| Sodium percarbonate | 13–22% |
| TAED | 1–8% |
| Carboxymethyl cellulose | 0–3% |
| Polymers (e.g. polycarboxylates and PVP) | 0–3% |
| Enzymes (calculated as pure enzyme protein) | 0.0001–0.1% |
| Minor ingredients (e.g. optical brightener, phosphonate, perfume) | 0–3% |

16) Detergent formulations as described in 1)–15) which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", Nature 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

Particular forms of dishwashing detergent compositions within the scope of the invention include:

1) POWDER AUTOMATIC DISHWASHING COMPOSITION

| | |
|---|---|
| Nonionic surfactant | 0.4–2.5% |
| Sodium metasilicate | 0–20% |
| Sodium disilicate | 3–20% |
| Sodium triphosphate | 20–40% |
| Sodium carbonate | 0–20% |
| Sodium perborate | 2–9% |
| Tetraacetylethylenediamine (TAED) | 1–4% |
| Sodium sulphate | 5–33% |
| Enzymes | 0.0001–0.1% |

2) POWDER AUTOMATIC DISHWASHING COMPOSITION

| | |
|---|---|
| Nonionic surfactant (e.g. alcohol ethoxylate) | 1–2% |
| Sodium disilicate | 2–30% |
| Sodium carbonate | 10–50% |
| Sodium phosphonate | 0–5% |
| Trisodium citrate dihydrate | 9–30% |
| Nitrilotrisodium acetate (NTA) | 0–20% |
| Sodium perborate monohydrate | 5–10% |
| Tetraacetylethylenediamine (TAED) | 1–2% |
| Polyacrylate polymer (e.g. maleic acid/acrylic acid copolymer) | 6–25% |
| Enzymes | 0.0001–0.1% |
| Perfume | 0.1–0.5% |
| Water | 5–10 |

3) POWDER AUTOMATIC DISHWASHING COMPOSITION

| | |
|---|---|
| Nonionic surfactant | 0.5–2.0% |
| Sodium disilicate | 25–40% |
| Sodium citrate | 30–55% |
| Sodium carbonate | 0–29% |
| Sodium bicarbonate | 0–20% |
| Sodium perborate monohydrate | 0–15% |
| Tetraacetylethylenediamine (TAED) | 0–6% |
| Maleic acid/acrylic acid copolymer | 0–5% |
| Clay | 1–3% |
| Poly(amino acids) | 0–20% |
| Sodium polyacrylate | 0–8% |
| Enzymes | 0.0001–0.1% |

4) POWDER AUTOMATIC DISHWASHING COMPOSITION

| | |
|---|---|
| Nonionic surfactant | 1–2% |
| Zeolite MAP | 15–42% |
| Sodium disilicate | 30–34% |
| Sodium citrate | 0–12% |
| Sodium carbonate | 0–20% |
| Sodium perborate monohydrate | 7–15% |
| Tetraacetylethylenediamine (TAED) | 0–3% |
| Polymer | 0–4% |
| Maleic acid/acrylic acid copolymer | 0–5% |
| Organic phosphonate | 0–4% |
| Clay | 1–2% |
| Enzymes | 0.0001–0.1% |
| Sodium sulphate | Balance |

5) POWDER AUTOMATIC DISHWASHING COMPOSITION

| | |
|---|---|
| Nonionic surfactant | 1–7% |
| Sodium disilicate | 18–30% |
| Trisodium citrate | 10–24% |
| Sodium carbonate | 12–20% |
| Monopersulphate (2 $KHSO_5$·$KHSO_4$·$K_2SO_4$) | 15–21% |
| Bleach stabilizer | 0.1–2% |
| Maleic acid/acrylic acid copolymer | 0–6% |
| Diethylenetriaminepentaacetate, pentasodium salt | 0–2.5% |
| Enzymes | 0.0001–0.1% |
| Sodium sulphate, water | Balance |

6) POWDER AND LIQUID DISHWASHING COMPOSITION WITH CLEANING SURFACTANT SYSTEM

| | |
|---|---|
| Nonionic surfactant | 0–1.5% |
| Octadecyl dimethylamine N-oxide dihydrate | 0–5% |
| 80:20 wt. C18/C16 blend of octadecyl dimethylamine N-oxide dihydrate and hexadecyldimethyl amine N-oxide dihydrate | 0–4% |
| 70:30 wt. C18/C16 blend of octadecyl bis (hydroxyethyl)amine N-oxide anhydrous and hexadecyl bis (hydroxyethyl)amine N-oxide anhydrous | 0–5% |
| $C_{13}$–$C_{15}$ alkyl ethoxysulfate with an average degree of ethoxylation of 3 | 0–10% |
| $C_{12}$–$C_{15}$ alkyl ethoxysulfate with an average degree of ethoxylation of 3 | 0–5% |
| $C_{13}$–$C_{15}$ ethoxylated alcohol with an average degree of ethoxylation of 12 | 0–5% |
| A blend of $C_{12}$–$C_{15}$ ethoxylated alcohols with an average degree of ethoxylation of 9 | 0–6.5% |
| A blend of $C_{13}$–$C_{15}$ ethoxylated alcohols with an average degree of ethoxylation of 30 | 0–4% |
| Sodium disilicate | 0–33% |
| Sodium tripolyphosphate | 0–46% |
| Sodium citrate | 0–28% |
| Citric acid | 0–29% |
| Sodium carbonate | 0–20% |
| Sodium perborate monohydrate | 0–11.5% |
| Tetraacetylethylenediamine (TAED) | 0–4% |
| Maleic acid/acrylic acid copolymer | 0–7.5% |
| Sodium sulphate | 0–12.5% |
| Enzymes | 0.0001–0.1% |

7) NON-AQUEOUS LIQUID AUTOMATIC DISHWASHING COMPOSITION

| | |
|---|---|
| Liquid nonionic surfactant (e.g. alcohol ethoxylates) | 2.0–10.0% |
| Alkali metal silicate | 3.0–15.0% |
| Alkali metal phosphate | 20.0–40.0% |
| Liquid carrier selected from higher glycols, polyglycols, polyoxides, glycolethers | 25.0–45.0% |
| Stabilizer (e.g. a partial ester of phosphoric acid and a $C_{16}$–$C_{18}$ alkanol) | 0.5–7.0% |
| Foam suppressor (e.g. silicone) | 0–1.5% |
| Enzymes | 0.0001–0.1% |

8) NON-AQUEOUS LIQUID DISHWASHING COMPOSITION

| | |
|---|---|
| Liquid nonionic surfactant (e.g. alcohol ethoxylates) | 2.0–10.0% |
| Sodium silicate | 3.0–15.0% |
| Alkali metal carbonate | 7.0–20.0% |
| Sodium citrate | 0.0–1.5% |
| Stabilizing system (e.g. mixtures of finely divided silicone and low molecular weight dialkyl polyglycol ethers) | 0.5–7.0% |
| Low molecule weight polyacrylate polymer | 5.0–15.0% |
| Clay gel thickener (e.g. bentonite) | 0.0–10.0% |
| Hydroxypropyl cellulose polymer | 0.0–0.6% |
| Enzymes | 0.0001–0.1% |
| Liquid carrier selected from higher lycols, polyglycols, polyoxides and glycol ethers | Balance |

9) THIXOTROPIC LIQUID AUTOMATIC DISHWASHING COMPOSITION

| | |
|---|---|
| $C_{12}$–$C_{14}$ fatty acid | 0–0.5% |
| Block co-polymer surfactant | 1.5–15.0% |
| Sodium citrate | 0–12% |
| Sodium tripolyphosphate | 0–15% |
| Sodium carbonate | 0–8% |
| Aluminum tristearate | 0–0.1% |
| Sodium cumene sulphonate | 0–1.7% |
| Polyacrylate thickener | 1.32–2.5% |
| Sodium polyacrylate | 2.4–6.0% |
| Boric acid | 0–4.0% |
| Sodium formate | 0–0.45% |
| Calcium formate | 0–0.2% |
| Sodium n-decydiphenyl oxide disulphonate | 0–4.0% |
| Monoethanol amine (MEA) | 0–1.86% |
| Sodium hydroxide (50%) | 1.9–9.3% |
| 1,2-Propanediol | 0–9.4% |
| Enzymes | 0.0001–0.1% |
| Suds suppressor, dye, perfumes, water | Balance |

10) LIQUID AUTOMATIC DISHWASHING COMPOSITION

| | |
|---|---|
| Alcohol ethoxylate | 0–20% |
| Fatty acid ester sulphonate | 0–30% |
| Sodium dodecyl sulphate | 0–20% |
| Alkyl polyglycoside | 0–21% |
| Oleic acid | 0–10% |
| Sodium disilicate monohydrate | 18–33% |
| Sodium citrate dihydrate | 18–33% |
| Sodium stearate | 0–2.5% |
| Sodium perborate monohydrate | 0–13% |
| Tetraacetylethylenediamine (TAED) | 0–8% |
| Maleic acid/acrylic acid copolymer | 4–8% |
| Enzymes | 0.0001–0.1% |

11) LIQUID AUTOMATIC DISHWASHING COMPOSITION CONTAINING PROTECTED BLEACH PARTICLES

| | |
|---|---|
| Sodium silicate | 5–10% |
| Tetrapotassium pyrophosphate | 15–25% |
| Sodium triphosphate | 0–2% |
| Potassium carbonate | 4–8% |
| Protected bleach particles, e.g. chlorine | 5–10% |
| Polymeric thickener | 0.7–1.5% |
| Potassium hydroxide | 0–2% |
| Enzymes | 0.0001–0.1% |
| Water | Balance |

11) Automatic dishwashing compositions as described in 1), 2), 3), 4), 6) and 10), wherein perborate is replaced by percarbonate.

12) Automatic dishwashing compositions as described in 1)–6) which additionally contain a manganese catalyst. The manganese catalyst may, e.g., be one of the compounds described in "Efficient manganese catalysts for low-temperature bleaching", Nature 369, 1994, pp. 637–639.

An α-amylase variant of the invention may be incorporated in concentrations conventionally employed in detergents. It is at present contemplated that, in the detergent composition of the invention, the α-amylase variant may be added in an amount corresponding to 0.00001–1 mg (calculated as pure enzyme protein) of α-amylase per liter of wash/dishwash liquor.

The present invention is further described with reference to the appended drawing, in which:

BRIEF DESCRIPTION OF THE DRAWINGS

FIG. 1 is an alignment of the amino acid sequences of four parent α-amylases in the context of the invention. The numbers on the extreme left designate the respective amino acid sequences as follows:

1: the amino acid sequence shown in SEQ ID No. 1;
2: the amino acid sequence shown in SEQ ID No. 2;
3: the amino acid sequence shown in SEQ ID No. 3; and
4: the amino acid sequence shown in SEQ ID No. 7.

The numbers on the extreme right of the figure give the running total number of amino acids for each of the sequences in question. It should be noted that for the sequence numbered 3 (corresponding to the amino acid sequence shown in SEQ ID No. 3), the alignment results in "gaps" at the positions corresponding to amino acid No. 1 and amino acid No. 175, respectively, in the sequences numbered 1 (SEQ ID No. 1), 2 (SEQ ID No. 2) and 4 (SEQ ID No. 7).

Figure 2:
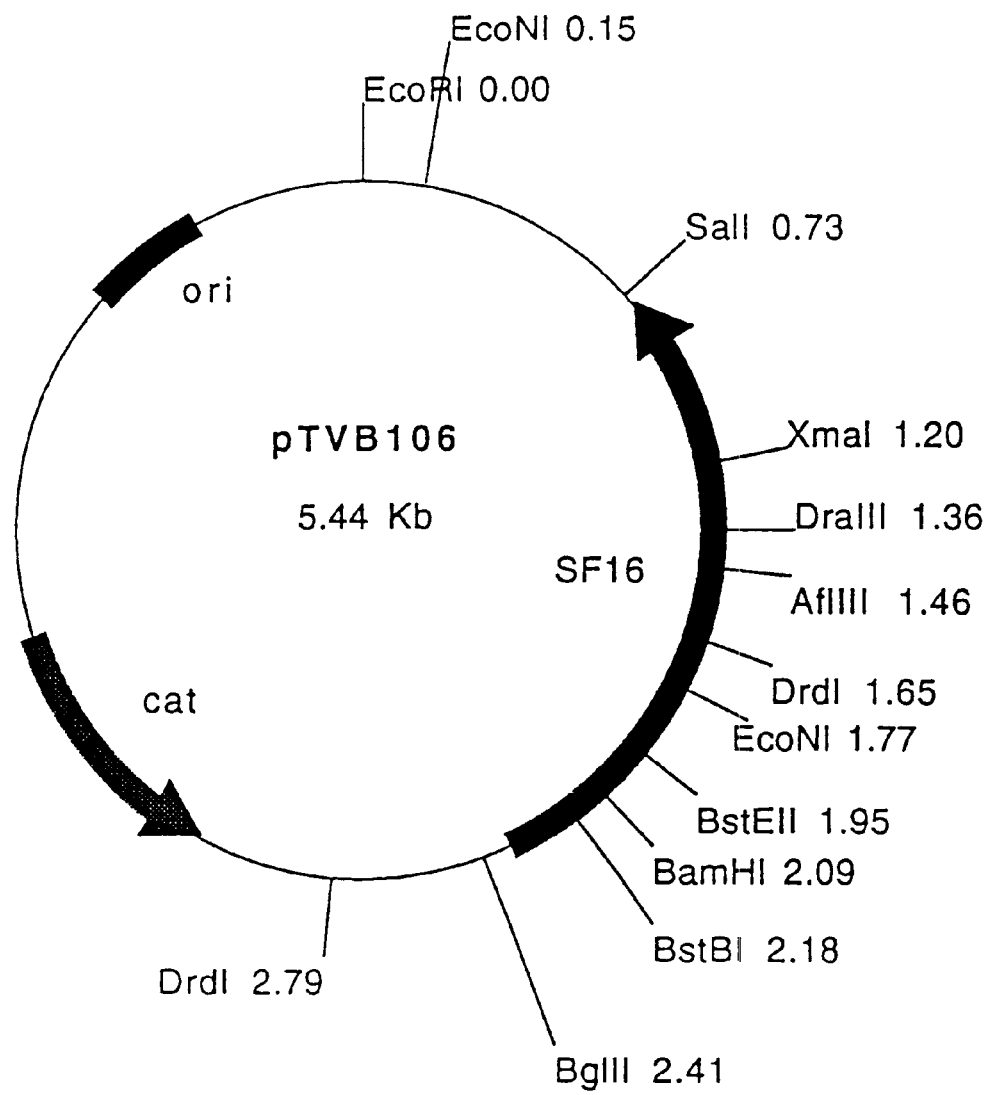
Figure 3:
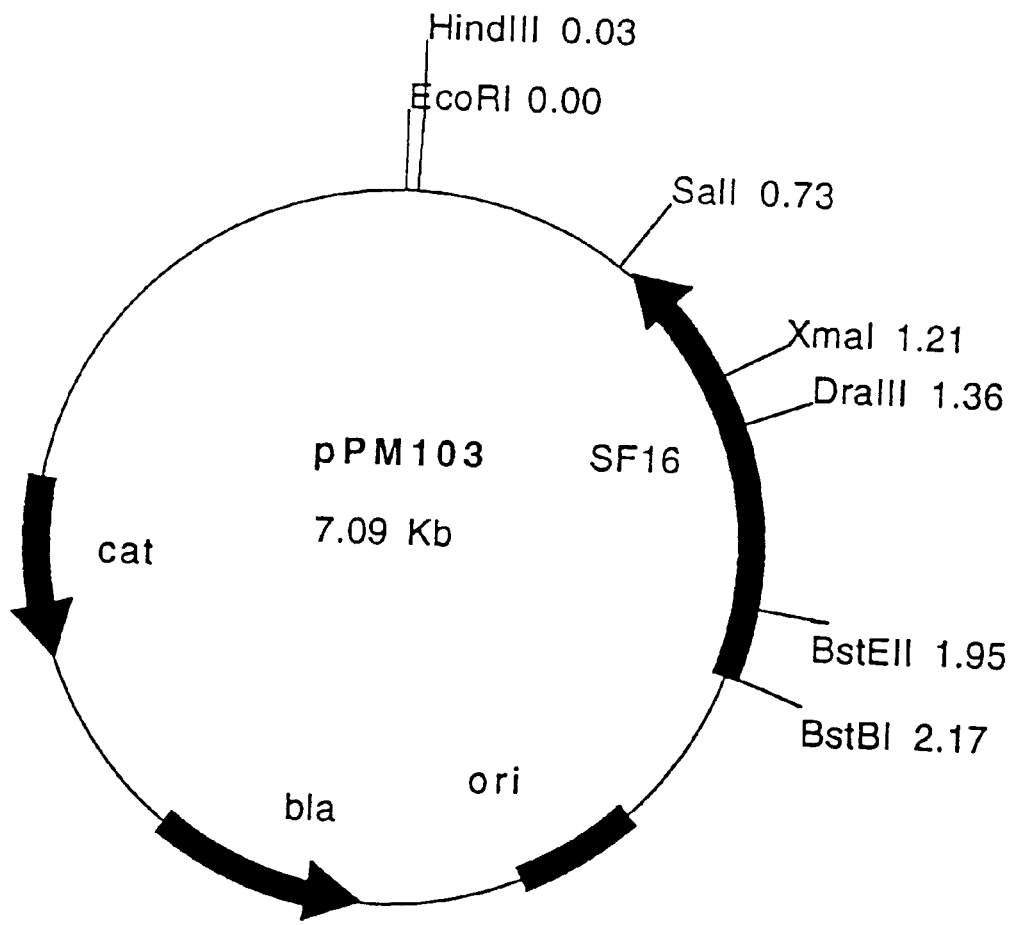
Figure 4:
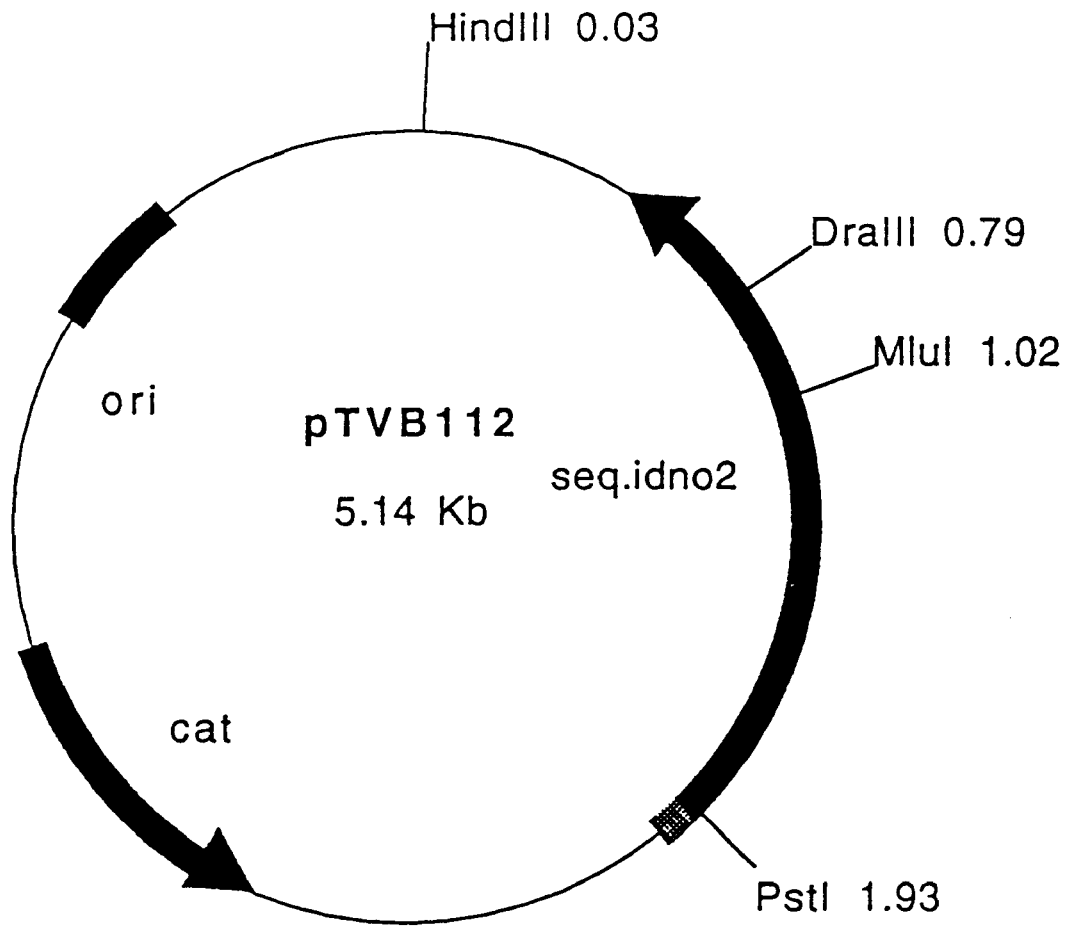
Figure 5:
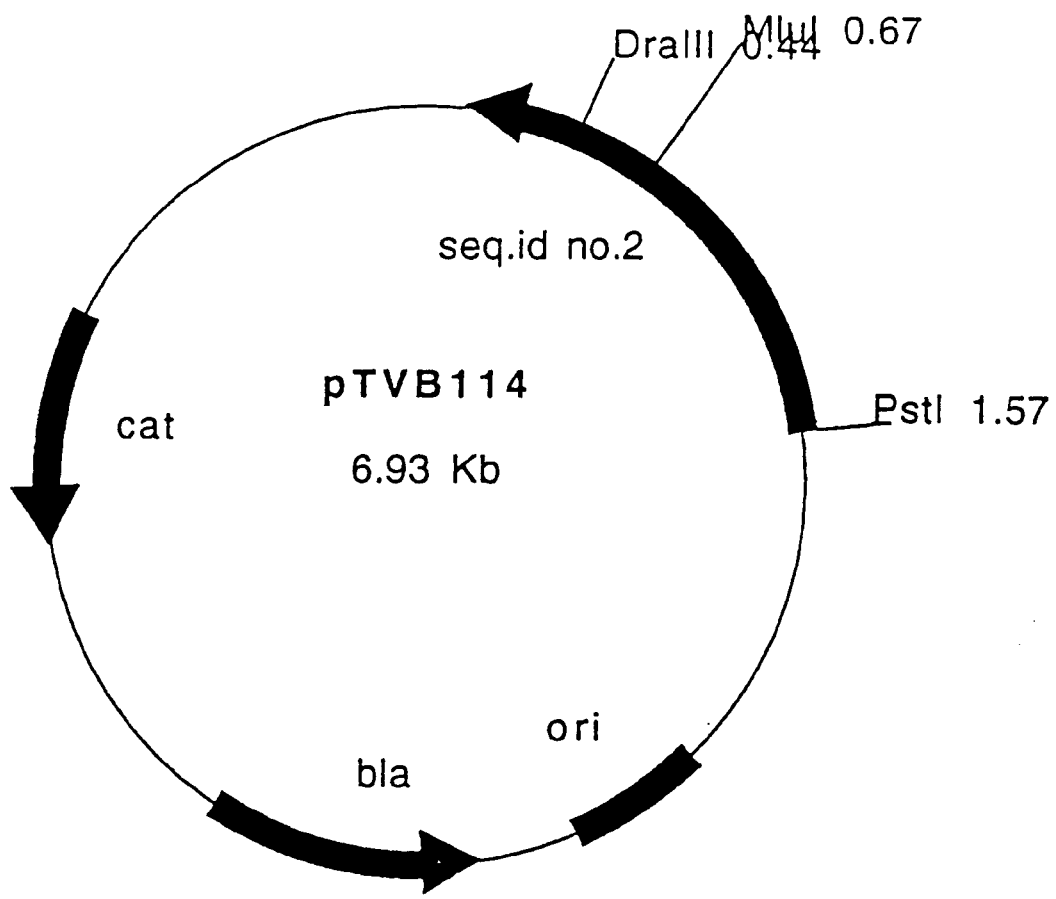

FIG. 2 is a restriction map of plasmid pTVB106.
FIG. 3 is a restriction map of plasmid pPM103.
FIG. 4 is a restriction map of plasmid pTVB112.
FIG. 5 is a restriction map of plasmid pTVB114.

EXPERIMENTAL SECTION

The preparation, purification and sequencing of the parent α-amylases having the amino acid sequences shown in SEQ ID No. 1 and SEQ ID No. 2 (from Bacillus strains NCIB 12512 and NCIB 12513, respectively) is described in WO 95/26397. The pI values and molecular weights of these two parent α-amylases (given in WO 95/26397) are as follows:

SEQ ID No. 1: pI about 8.8–9.0 (determined by isoelectric focusing on LKB Ampholine™ PAG plates); molecular weight approximately 55 kD (determined by SDS-PAGE).

SEQ ID No. 2: pI about 5.8 (determined by isoelectric focusing on LKB Ampholine™ PAG plates); molecular weight approximately 55 kD (determined by SDS-PAGE).

Purification of α-amylase Variants of the Invention

The construction and expression of variants according to the invention is described in Example 2, below. The purification of variants of the invention is illustrated here with reference to variants of the amino acid sequences shown in SEQ ID No. 1 and SEQ ID No. 2, respectively:

Purification of SEQ ID No. 1 variants (pI approx. 9.0):
The fermentation liquid containing the expressed α-amylase variant is filtered, and ammonium sulfate is added to a concentration of 15% of saturation. The liquid is then applied onto a hydrophobic column (Toyopearl butyl/TOSOH). The column is washed with 20 mM dimethylglutaric acid buffer, pH 7.0. The α-amylase is bound very tightly, and is eluted with 25% w/w 2-propanol in 20 mM dimethylglutaric acid buffer, pH 7.0. After elution, the 2-propanol is removed by evaporation and the concentrate is applied onto a cation exchanger (S-Sepharose™ FF, Pharmacia, Sweden) equilibrated with 20 mM dimethylglutaric acid buffer, pH 6.0.

The amylase is eluted using a linear gradient of 0–250 mM NaCl in the same buffer. After dialysis against 10 mM borate/KCl buffer, pH 8.0, the sample is adjusted to pH 9.6 and applied to an anion exchanger (Q-Sepharose™ FF, Pharmacia) equilibrated with 10 mM borate/KCl buffer, pH 9.6. The amylase is eluted using a linear gradient of 0–250 mM NaCl. The pH is adjusted to 7.5. The α-amylase is pure as judged by rSDS-PAGE. All buffers contain 2 mM $CaCl_2$ in order to stabilize the amylase.

Purification of SEQ ID No. 2 variants (pI approx. 5,8):
The fermentation liquid containing the expressed α-amylase variant is filtered, and ammonium sulfate is added to a concentration of 15% of saturation. The liquid is then applied onto a hydrophobic column (Toyopearl butyl/TOSOH). The bound amylase is eluted with a linear gradient of 15%–0% w/w ammonium sulfate in 10 mM Tris buffer, pH 8.0. After dialysis of the eluate against 10 mM borate/KCl buffer, pH 8.0, the liquid is adjusted to pH 9.6 and applied onto an anion exchanger (Q-Sepharose™ FF, Pharmacia) equilibrated with the same buffer. The amylase is step-eluted using 150 mM NaCl.

After elution the amylase sample is dialyzed against the same buffer, pH 8.0, in order to remove the NaCl. After dialysis, the pH is adjusted to 9.6 and the amylase is bound once more onto the anion exchanger. The amylase is eluted using a linear gradient of 0–250 mM NaCl. The pH is adjusted to 7.5. The amylase is pure as judged by rSDS-PAGE. All buffers contain 2 mM $CaCl_2$ in order to stabilize the amylase.

Determination of α-amylase Activity

α-Amylase activity is determined by a method employing Phadebas™ tablets as substrate. Phadebas tablets (Phadebas™ Amylase Test, supplied by Pharmacia Diagnostic) contain a cross-linked insoluble blue-colored starch polymer which has been mixed with bovine serum albumin and a buffer substance and tabletted.

For the determination of every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The α-amylase to be tested is diluted in x ml of 50 mM Britton-Robinson buffer. 1 ml of this α-amylase solution is added to the 5 ml 50 mM Britton-Robinson buffer. The starch is hydrolyzed by the α-amylase giving soluble blue fragments. The absorbance of the resulting blue solution, measured spectrophotometrically at 620 nm, is a function of the α-amylase activity.

It is important that the measured 620 nm absorbance after 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion.

Under a specified set of conditions (temp., pH, reaction time, buffer conditions) 1 mg of a given α-amylase will hydrolyze a certain amount of substrate and a blue color will be produced. The color intensity is measured at 620 nm. The measured absorbance is directly proportional to the specific activity (activity/mg of pure α-amylase protein) of the α-amylase in question under the given set of conditions. Thus testing different α-amylases of interest (including a reference α-amylase, in this case the parent α-amylase in question) under identical conditions, the specific activity of each of the α-amylases at a given temperature and at a given pH can be compared directly, and the ratio of the specific activity of each of the α-amylases of interest relative to the specific activity of the reference α-amylase can be determined.

Mini Dishwashing Assay

The following mini dishwashing assay was used: A suspension of starchy material was boiled and cooled to 20° C. The cooled starch suspension was applied on small, individually identified glass plates (approx. 2×2 cm) and dried at a temperature of ca. 140° C. in a drying cabinet. The individual plates were then weighed. For assay purposes, a solution of standard European-type automatic dishwashing detergent (5 g/l) having a temperature of 55° C. was prepared. The detergent was allowed a dissolution time of 1 minute, after which the α-amylase in question was added to the detergent solution (contained in a beaker equipped with magnetic stirring) so as to give an enzyme concentration of 0.5 mg/l. At the same time, the weighed glass plates, held in small supporting clamps, were immersed in a substantially vertical position in the α-amylase/detergent solution, which was then stirred for 15 minutes at 55° C. The glass plates were then removed from the α-amylase/detergent solution, rinsed with distilled water, dried at 60° C. in a drying cabinet and re-weighed. The performance of the α-amylase in question [expressed as an index relative to a chosen reference α-amylase (index 100)—in the example below (Example 1) the parent α-amylase having the amino acid sequence shown in SEQ ID No. 1] was then determined from the difference in weight of the glass plates before and after treatment, as follows:

Index=weight loss for plate treated with α-amylase/weight loss for plate treated with reference·100

The following examples further illustrate the present invention. They are not intended to be in any way limiting to the scope of the invention as claimed.

EXAMPLE 1

Mini Dishwashing Test of Variants of Parent α-amylase Having the Amino Acid Sequence Shown in SEQ ID No. 1

The above-described mini dishwashing test was performed at pH 10.5 with the parent α-amylase having the amino acid sequence shown in SEQ ID No. 1 and the following variants thereof (the construction and purification of which is described below): T183*+G184*; Y243F; and K269R. The test gave the following results:

| | |
|---|---|
| Parent (SEQ ID No. 1) | Index: 100 |
| T183* + G184* | Index: 120 |
| Y243F | Index: 120 |
| K269R | Index: 131 |

It is apparent that the each of the tested variants T183*+G184* (which exhibits, inter alia, higher thermal stability than the parent α-amylase), Y243F (which exhibits lower calcium ion dependency than the parent α-amylase) and K269R (which exhibits lower calcium ion dependency and higher stability at high pH than the parent α-amylase) exhibits significantly improved dishwashing performance relative to the parent α-amylase.

EXAMPLE 2

Construction of Variants of the Parent α-amylases Having the Amino Acid Sequences Shown in SEQ ID No. 1 and SEQ ID No. 2, Respectively Primers: DNA primers employed in the construction of variants as described below include the following [all DNA primers are written in the direction from 5' to 3' (left to right); P denotes a 5' phosphate]:

```
#7113:
GCT GCG GTG ACC TCT TTA AAA AAT AAC GGC              (SEQ ID NO:8)

Y296:
CC ACC GCT ATT AGA TGC ATT GTA C                     (SEQ ID NO:9)

#6779:
CTT ACG TAT GCA GAC GTC GAT ATG GAT CAC CC           (SEQ ID NO:10)

#6778:
G ATC CAT ATC GAC GTC TGC ATA CGT AAG ATA GTC        (SEQ ID NO:11)

#3811:
TT A(C/G)G GGC AAG GCC TGG GAC TGG                   (SEQ ID NO:12)

#7449:
C CCA GGC CTT GCC C(C/G)T AAA TTT ATA TAT TTT GTT TTG (SEQ ID NO:13)

#3810:
G GTT TCG GTT CGA AGG ATT CAC TTC TAC CGC            (SEQ ID NO:14)

#7450:
GCG GTA GAA GTG AAT CCT TCG AAC CGA AAC CAG          (SEQ ID NO:15)

B1:
GGT ACT ATC GTA ACA ATG GCC GAT TGC TGA CGC TGT TAT TTG C (SEQ ID NO:16)

#6616:
P CTG TGA CTG GTG AGT ACT CAA CCA AGT C              (SEQ ID NO:17)

#8573:
CTA CTT CCC AAT CCC AAG CTT TAC CTC GGA ATT TG       (SEQ ID NO:18)

#8569:
CAA ATT CCG AGG TAA AGC TTG GGA TTG GGA AGT AG       (SEQ ID NO:19)

#8570:
TTG AAC AAC CGT TCC ATT AAG AAG                      (SEQ ID NO:20)
```

A: Construction of Variants of the Parent α-amylase Having the Amino Acid Sequence Shown in SEQ ID No. 1

Description of plasmid pTVB106: The parent α-amylase having the amino acid sequence shown in SEQ ID No. 1 and variants thereof are expressed from a plasmid-borne gene, SF16, shown in FIG. 2. The plasmid, pTVB106, contains an origin of replication obtained from plasmid pUJB110 (Gryczan et al., 1978) and the cat gene conferring resistance towards chloramphenicol. Secretion of the amylase is aided by the Termamyl™ signal sequence that is fused precisely, i.e. codon No.1 of the mature protein, to the gene encoding the parent α-amylase having the nucleotide and amino acid sequence (mature protein) shown in SEQ ID No. 4 and SEQ ID No. 1, respectively. The Termamyl promoter initiates transcription of the gene.

Plasmid pTVB106 is similar to pDN1528 (see laid-open Danish patent application No. 1155/94). Some unique restriction sites are indicated on the plasmid map in FIG. 2, including BstBI, BamHI, BstEII, EcoM, DrdI, AflIII, DraIII, XmaI, SalI and BglII.

Construction of variant M202T: The PCR overlap extension mutagenesis method is used to construct this variant (Higuchi et al., 1988). An approximately 350 bp DNA fragment of pTVB106 is amplified in a PCR reaction A using primers #7113 and mutagenic primer #6778. In a similar PCR reaction B, an approximately 300 bp DNA fragment is amplified using primers Y296 and #6779. The complete DNA fragment spanning the mutation site (M202) from primer #7113 to primer Y296 is amplified in PCR C using these primers and purified DNA fragments from reactions A and B.

PCR C DNA is digested with restriction endonucleases BstEII and AflIII, and the 480 bp fragment is ligated with plasmid pTVB106 digested with the same enzymes and transformed into a low-protease and low-amylase *Bacillus subtilis* strain (e.g. strain SHA273 mentioned in WO 92/11357).

Other M202 variants are constructed in a similar manner.

Construction of variants T183*+G184* and R181*+G182*: The PCR overlap extension mutagenesis method is used to construct these variants (Higuchi et al., 1988). The mutagenic oligonucleotides are synthesized using a mixture (equal parts) of C and G in one position; two different mutations can therefore be constructed by this procedure. An approximately 300 bp DNA fragment of pTVB106 is amplified in a PCR reaction A using primers #7113 and mutagenic primer #7449. In a similar PCR reaction B, an approximately 400 bp DNA fragment is amplified using primers Y296 and #3811. The complete DNA fragment spanning the mutation site (amino acids 181–184) from primer #7113 to primer Y296 is amplified in PCR C using these primers and purified DNA fragments from reactions A and B.

PCR C DNA is digested with restriction endonucleases BstEII and AflIII and the 480 bp fragment is ligated with plasmid pTVB106 digested with the same enzymes and transformed into a low-protease and low-amylase *B. subtilis* strain (e.g. strain SHA273 mentioned in WO 92/11357). Sequencing of plasmid DNA from these transformants identifies the two correct mutations: i.e. R181*+G182* and T183*+G184*.

Construction of variant R124P: The PCR overlap extension mutagenesis method is used to construct this variant in a manner similar to the construction of variant M202T (vide supra). PCR reaction A (with primers #3810 and B1) generates an approximately 500 bp fragment, and PCR reaction B (primers 7450 and Y296) generates an approximately 550 bp fragment. PCR reaction C based on the product of PCR reaction A and B and primers B1 and Y296 is digested with restriction endonucleases BstEII and AflIII, and the resulting 480 bp fragment spanning amino acid position 124 is subcloned into pTVB106 digested with the same enzymes and transformed into *B. subtilis* as previously described.

Construction of variant R124P+T183*+G184*: For the construction of the variant combining the R124P and the T183*+G184* mutations, two EcoNI restriction sites (one located at position 1.774 kb, i.e. between the R124P mutation and the T183*+G184* mutation, and one located at position 0.146 kb) were utilized. The approximately 1630 bp EcoNI fragment of the pTVB106-like plasmid containing the T183*+G184* mutation was subcloned into the vector part (approximately 3810 bp DNA fragment containing the origin of replication) of another pTVB106-like plasmid containing the R124P mutation digested with the same enzyme. Transformation into *Bacillus subtilis* was carried out as previously described.

Construction of variants G182*+G184*; R181*+T183*; Y243F; K269R; and L351C+M430C: These variants were constructed as follows:

A specific mutagenesis vector containing a major part of the coding region for the amino acid sequence shown in SEQ ID No. 1 was prepared. The important features of this vector (which is denoted pPM103) include an origin of replication derived from the pUC plasmid, the cat gene conferring resistance towards chloramphenicol and a frameshift-mutation-containing version of the bla gene, the wild-type version of which normally confers resistance towards ampicillin (amp$^R$ phenotype). This mutated version of the bla gene results in an amp$^S$ phenotype. The plasmid pPM103 is shown in FIG. 3, and the *E. coli* origin of replication, the 5'-truncated version of the SF16 amylase gene, and ori, bla, cat and selected restriction sites are indicated on the plasmid.

Mutations are introduced in the gene of interest as described by Deng and Nickoloff [*Anal. Biochem.* 200 (1992), pp. 81–88], except that plasmids with the "selection primer" (#6616) incorporated are selected based on the amp$^R$ phenotype of transformed *E. coli* cells harboring a plasmid with a repaired bla gene instead of using the selection by restriction-enzyme digestion outlined by Deng and Nickoloff. Chemicals and enzymes used for the mutagenesis were obtained from the Chameleon™ mutagenesis kit from Stratagene (catalogue number 200509).

After verification of the DNA sequence in variant plasmids, the truncated gene containing the desired alteration is subcloned from the pPM103-like plasmid into pTVB106 as an approximately 1440 bp BstBI-SalI fragment and transformed into *Bacillus subtilis* for expression of the variant enzyme.

For the construction of the pairwise deletion variant G182*+G184*, the following mutagenesis primer was used:
P CTC TGT ATC GAC TTC CCA GTC CCA AGC TTT TGT CCT GAA TTT ATA TAT TTT GTT TTG AAG (SEQ ID NO: 21)

For the construction of the pairwise deletion variant R181*+T183*, the following mutagenesis primer was used:
P CTC TGT ATC GAC TTC CCA GTC CCA AGC TTT GCC TCC GAA TTT ATA TAT TTT GTT TTG AAG (SEQ ID NO: 22)

For the construction of the substitution variant Y243F, the following mutagenesis primer was used:
P ATG TGT AAG CCA ATC GCG AGT AAA GCT AAA TTT TAT ATG TTT CAC TGC ATC (SEQ ID NO: 23)

For the construction of the substitution variant K269R, the following mutagenesis primer was used:
P GC ACC AAG GTC ATT TCG CCA GAA TTC AGC CAC TG (SEQ ID NO: 24)

For the construction of the pairwise substitution variant L351C+M430C, the following mutagenesis primers were used simultaneously:

1) P TGT CAG AAC CAA CGC GTA TGC ACA TGG TTT AAA CCA TTG (SEQ ID NO: 25)
2) P ACC ACC TGG ACC ATC GCT GCA GAT GGT GGC AAG GCC TGA ATT (SEQ ID NO: 26)

Construction of variant L351C+M430C+T183*+G184*: This variant was constructed by combining the L351C+M430C pairwise substitution mutation and the T183*+G184*pairwise deletion mutation by subcloning an approximately 1430 bp HindIII-AflIII fragment containing L351C+M430C into a pTVB106-like plasmid (with the T183*+G184* mutations) digested with the same enzymes.

Construction of variant Y243F+T183*+G184*: This variant was constructed by combining the Y243F mutation and the T183*+G184* mutation by subcloning an approximately 1148 bp DrdI fragment containing T183*+G184* into a pTVB106-like plasmid (with the Y243 mutation) digested with the same enzyme.

Bacillus subtilis transformants were screened for α-amylase activity on starch-containing agar plates and the presence of the correct mutations was checked by DNA sequencing.

Construction of variant Y243F+T183*+G184*+L351C+M430C: The L351C+M430C pairwise substitution mutation was subcloned as an approximately 470 bp XmaI-SalI fragment into a pTVB106-like vector (containing Y243F+T183*+G184*) digested with the same enzymes.

Construction of variant Y243F+T183*+G184*+L351C+M430C+Q391E+K444Q: A pPM103-like vector containing the mutations Y243F+T183*+G184*+L351C+M430C was constructed by substituting the truncated version of SF16 in pPM103 with the approximately 1440 bp BstB1-SalI fragment of the pTVB106-like vector containing the five mutations in question. The Q391E and K444Q mutations were introduced simultaneously into the pPM103-like vector (containing Y243F+T183*+G184*+L351C+M430C) by the use of the following two mutagenesis primers in a manner similar to the previously described mutagenesis on pPM103:
P GGC AAA AGT TTG ACG TGC CTC GAG AAG AGG GTC TAT (SEQ ID NO: 27)
P TTG TCC CGC TTT ATT CTG GCC AAC ATA CAT CCA TTT (SEQ ID NO: 28)

B: Construction of Variants of the Parent α-amylase Having the Amino Acid Sequence Shown in SEQ ID No. 2

Description of plasmid pTVB112: A vector, denoted pTVB112, to be used for the expression in *B. subtilis* of the α-amylase having the amino acid sequence shown in SEQ ID No. 2 was constructed. This vector is very similar to pTVB106 except that the gene encoding the mature α-amylase of SEQ ID No. 2 is inserted between the PstI and the HindIII sites in pTVB106. Thus, the expression of this α-amylase (SEQ ID No. 2) is also directed by the amyL promoter and signal sequence. The plasmid pTVB112 is shown in FIG. 4.

Construction of variant D183*+G184*: The construction of this variant was achieved using the PCR overlap extension mutagenesis method referred to earlier (vide supra). Primers #8573 and B1 were used in PCR reaction A, and primers #8569 and #8570 were used in PCR reaction B. The purified fragments from reaction A and reaction B and primers 1B and #8570 were used in PCR reaction C, resulting in an approximately 1020 bp DNA fragment. This fragment was digested with restriction endonucleases PstI and MluI, and subcloned into the expression vector and transformed into *B. subtilis*.

Construction of further variants: By analogy with the construction (vide supra) of the plasmid pPM103 used in the production of mutants of the amino acid sequence of SEQ ID No. 1, a plasmid (denoted pTVB114; shown in FIG. 5) was constructed for the continued mutagenesis on variant D183*+G184* (SEQ.ID No. 2). Mutations were introduced in pTVB114 (SEQ ID No. 2; D183*+G184*) in a manner similar to that for pPM103 (SEQ ID No. 1).

For the construction of the pairwise deletion variants R181*+D183* and R181*+G182*, it was chosen to alter the flanking amino acids in the variant D183*+G184* instead of deleting the specified amino acids in the wild type gene for SEQ ID No. 2. The following mutagenesis primer was used for the mutagenesis with pTVB114 as template:
PCC CAA TCC CAA GCT TTA CCA (T/C)CG AAC TTG TAG ATA CG (SEQ ID NO: 29)

The presence of a mixture of two bases (T/C) at one position allows for the presence of two different deletion flanking amino acid based on one mutagenesis primer. DNA sequencing of the resulting plasmids verifies the presence of either the one or the other mutation. The mutated gene of interest is subcloned as a PstI-DraIII fragment into pTVB112 digested with the same enzymes and transformed into *B. subtilis*.

For the construction of G182*+G184* and R181*+G184*, the following mutagenesis primer was used with pTVB114 as template:
PCC CAA TCC CAA GCT TTA TCT C(C/G)G AAC TTG TAG ATA CG (SEQ ID NO: 30)

As before, the presence of a mixture of two bases (C/G) at one position allows for the presence of two different deletion flanking amino acid based on one mutagenesis primer. DNA sequencing of the resulting plasmids verifies the presence of either the one or the other mutation. The mutated gene of interest is subcloned as a PstI-DraIII fragment into pTVB112 digested with the same enzymes and transformed into *B. subtilis*.

For the construction of D1 83*+G184*+M202L the following mutagenesis primer was used:
PGA TCC ATA TCG ACG TCT GCA TAC AGT AAA TAA TC (SEQ ID NO: 31)

For the construction of D183*+G184*+M2021 the following mutagenesis primer was used:
PGA TCC ATA TCG ACG TCT GCA TAA ATT AAA TAA TC (SEQ ID NO: 32)

EXAMPLE 3

Determination of Oxidation Stability of M202 Substitution Variants of the Parent α-amylases Having the Amino Acid Sequences Shown in SEQ ID No. 1 and SEQ ID No. 2

A: Oxidation Stability of Variants of the Sequence in SEQ ID No. 1

The measurements were made using solutions of the respective variants in 50 mM Britton-Robinson buffer (50 mM acetic acid, 50 mM phosphoric acid, 50 mM boric acid. 0.1 mM $CaCl_2$, pH adjusted to the value of interest with NaOH), pH 9.0, to which hydrogen peroxide was added (at time t=0) to give a final concentration of 200 mM $H_2O_2$. The solutions were then incubated at 40° C. in a water bath.

After incubation for 5, 10, 15 and 20 minutes after addition of hydrogen peroxide, the residual α-amylase activity was measured using the Phadebas assay described above. The residual activity in the samples was measured using 50 mM Britton-Robinson buffer, pH 7.3, at 37° C. (see Novo analytical publication AF207-1/1, available on request from Novo Nordisk A/S). The decline in activity was measured relative to a corresponding reference solution of the same enzyme at 0 minutes which was not incubated with hydrogen peroxide (100% activity).

The percentage of initial activity as a function of time is shown in the table below for the parent enzyme (SEQ ID No. 1) and for the variants in question.

| Variant | % Activity after incubation for (minutes) | | | | |
|---|---|---|---|---|---|
| | 0 | 5 | 10 | 15 | 20 |
| M202L | 100 | 90 | 72 | 58 | 27 |
| M202F | 100 | 100 | 87 | 71 | 43 |
| M202A | 100 | 99 | 82 | 64 | 30 |
| M202I | 100 | 91 | 75 | 59 | 28 |
| M202T | 100 | 87 | 65 | 49 | 20 |
| M202V | 100 | 100 | 87 | 74 | 43 |
| M202S | 100 | 100 | 85 | 68 | 34 |
| Parent | 100 | 51 | 26 | 13 | 2 |

All the M202 substitution variants tested clearly exhibit significantly improved stability towards oxidation relative to the parent α-amylase (SEQ ID No. 1).

B: Oxidation Stability of Variants of the Sequence in SEQ ID No. 2

Measurements were made as described above using the parent α-amylase in question (SEQ ID No. 2), the variant M202L+D183*+G184*(designated L in the table below) and the variant M202I+D183*+G184* (designated I in the table below), respectively. In this case, incubation times (after addition of hydrogen peroxide) of 5, 10, 15 and 30 minutes were employed. As in the table above, the percentage of initial activity as a function of time is shown in the table below for the parent enzyme and for the variants in question.

| Variant | % Activity after incubation for (minutes) | | | | |
|---|---|---|---|---|---|
| | 0 | 5 | 10 | 15 | 30 |
| L | 100 | 91 | 85 | 71 | 43 |
| I | 100 | 81 | 61 | 44 | 18 |
| Parent | 100 | 56 | 26 | 14 | 4 |

The two "substitution+pairwise deletion" variants tested (which both comprise an M202 substitution) clearly exhibit significantly improved stability towards oxidation relative to the parent α-amylase (SEQ ID No. 2).

EXAMPLE 4
Determination of Thermal Stability of Variants of the Parent α-amylases Having the Amino Acid Sequences Shown in SEQ ID No. 1 and SEQ ID No. 2

A: Thermal Stability of Pairwise Deletion Variants of the Sequence in SEQ ID No. 1

Measurements were made using solutions of the respective variants in 50 mM Britton-Robinson buffer (vide supra), pH 9.0. The solutions were incubated at 65° C. in a water bath, and samples were withdrawn after incubation for the indicated periods of time. The residual α-amylase activity of each withdrawn sample was measured using the Phadebas assay, as described above. The decline in activity was measured relative to a corresponding reference solution of the same enzyme at 0 minutes which was not incubated (100% activity).

The percentage of initial activity as a function of time is shown in the table below for the parent enzyme (SEQ ID No. 1) and for the following pairwise deletion variants in question:

Variant 1: R181*+G182*
Variant 2: R181*+T183*
Variant 3: G182*+G184*
Variant 4: T183*+G184*
Variant 5: T183*+G184*+R124P

| Variant | % Activity after incubation for (minutes) | | | | | |
|---|---|---|---|---|---|---|
| | 0 | 5 | 10 | 15 | 30 | 45 | 60 |
| 1 | 100 | 81 | 66 | 49 | 24 | 14 | 8 |
| 2 | 100 | 80 | 53 | 39 | 17 | 8 | 3 |
| 3 | 100 | 64 | 40 | 28 | 10 | 4 | 2 |
| 4 | 100 | 64 | 43 | 34 | 20 | 8 | 5 |
| 5 | 100 | 78 | 73 | 66 | 57 | 47 | 38 |
| Parent | 100 | 13 | 2 | 0 | 0 | 0 | 0 |

It is apparent that all of the pairwise deletion variants tested exhibit significantly improved thermal stability relative to the parent α-amylase (SEQ ID No. 1), and that the thermal stability of Variant 5, which in addition to the pairwise deletion mutation of Variant 4 comprises the substitution R124P, is markedly higher than that of the other variants. Since calorimetric results for the substitution variant R124P (comprising only the substitution R124P) reveal an approximately 7° C. thermostabilization thereof relative to the parent α-amylase, it appears that the thermostabilizing effects of the mutation R124P and the pairwise deletion, respectively, reinforce each other.

B: Thermal Stability of Pairwise Deletion Variants of the Sequence in SEQ ID No. 2

Corresponding measurements were made for the parent enzyme (SEQ ID No. 2) and for the following pairwise deletion variants:

Variant A: D183*+G184*
Variant B: R181*+G182*
Variant C: G182*+G184*

| Variant | % Activity after incubation for (minutes) | | | | |
|---|---|---|---|---|---|
| | 0 | 5 | 10 | 15 | 30 |
| A | 100 | 87 | 71 | 63 | 30 |
| B | 100 | 113 | 85 | 76 | 58 |
| C | 100 | 99 | 76 | 62 | 34 |
| Parent | 100 | 72 | 55 | 44 | 18 |

Again, it is apparent that the pairwise deletion variants in question exhibit significantly improved thermal stability relative to the parent α-amylase (SEQ ID No. 2).

C: Thermal Stability of a Multi-combination Variant of the Sequence in SEQ ID No. 1

Corresponding comparative measurements were also made for the following variants of the amino acid sequence shown in SEQ ID No. 1:

Variant 4: T183*+G184*
Variant 6: L351C+M430C
Variant 7: Y243F
Variant 8: Q391E+K444Q
Variant 9: T183*+G184*+L351C+M430C+Y243F+Q391E+K444Q

| Variant | % Activity after incubation for (minutes) | | | | |
|---|---|---|---|---|---|
| | 0 | 5 | 10 | 15 | 30 |
| 4 | 100 | 66 | 41 | 22 | 7 |
| 6 | 100 | 87 | 73 | 65 | 43 |
| 7 | 100 | 14 | 2 | 1 | 0 |
| 8 | 100 | 69 | 46 | 31 | 14 |
| 9 | 100 | 92 | 93 | 89 | 82 |

Again, it appears that the thermostabilizing effect of multiple mutations, each of which has a thermostabilizing effect, is—at least qualitatively—cumulative.

EXAMPLE 5
Calcium-binding Affinity of α-amylase Variants of the Invention

Unfolding of amylases by exposure to heat or to denaturants such as guanidine hydrochloride is accompanied by a decrease in fluorescence. Loss of calcium ions leads to unfolding, and the affinity of a series of α-amylases for calcium can be measured by fluorescence measurements before and after incubation of each α-amylase (e.g. at a concentration of 10 µg/ml) in a buffer (e.g. 50 mM HEPES, pH 7) with different concentrations of calcium (e.g. in the range of 1 µM-100 mM) or of EGTA (e.g. in the range of 1–1000 µM) [EGTA=1,2-di(2-aminoethoxy)ethane-N,N,N', N'-tetraacetic acid] for a sufficiently long period of time (such as 22 hours at 55° C.).

The measured fluorescence F is composed of contributions form the folded and unfolded forms of the enzyme. The following equation can be derived to describe the dependence of F on calcium concentration ([Ca]):

$$F=[Ca]/(K_{diss}+[Ca])(\alpha_N-\beta_N\log([Ca]))+K_{diss}/(K_{diss}+[Ca])(\alpha_U-\beta_U\log([Ca]))$$

where $\alpha_N$ is the fluorescence of the native (folded) form of the enzyme, $\beta_N$ is the linear dependence of $\alpha_N$ on the logarithm of the calcium concentration (as observed experimentally), $\alpha_U$ is the fluorescence of the unfolded form and $\beta_U$ is the linear dependence of $\alpha_u$ on the logarithm of the calcium concentration. $K_{diss}$ is the apparent calcium-binding constant for an equilibrium process as follows:

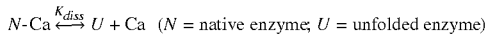
$N\text{-Ca} \overset{K_{diss}}{\longleftrightarrow} U + \text{Ca}$   ($N$ = native enzyme; $U$ = unfolded enzyme)

In fact, unfolding proceeds extremely slowly and is irreversible. The rate of unfolding is a dependent on calcium concentration, and the dependency for a given α-amylase provides a measure of the Ca-binding affinity of the enzyme. By defining a standard set of reaction conditions (e.g. 22 hours at 55° C.), a meaningful comparison of $K_{diss}$ for different α-amylases can be made. The calcium dissociation curves for α-amylases in general can be fitted to the equation above, allowing determination of the corresponding values of $K_{diss}$.

The following values for $K_{diss}$ were obtained for the parent α-amylases having the amino acid sequences shown in SEQ ID No. 1 and SEQ ID No. 2, and for the indicated α-amylase variants according to the invention (the parent α-amylase being indicated in parentheses):

| Variant | $K_{diss}$ (mol/l) |
|---|---|
| D183* + G184* (SEQ ID No. 2) | 1.2 (±0.5) × $10^{-4}$ |
| L351C + M430C + T183* + G184* (SEQ ID No. 1) | 1.7 (±0.5) × $10^{-3}$ |
| T183* + G184* (SEQ ID No. 1) | 4.3 (±0.7) × $10^{-3}$ |
| SEQ ID No. 2 (parent) | 4.2 (±1.2) × $10^{-2}$ |
| SEQ ID No. 1 (parent) | 3.5 (±1.1) × $10^{-1}$ |

It is apparent from the above that the calcium-binding affinity of the latter α-amylolytic enzymes decreases in a downward direction through the above table, i.e. that the pairwise deletion variant D183*+G184* (SEQ ID No. 2) binds calcium most strongly (i.e. has the lowest calcium dependency) whilst the parent α-amylase of SEQ ID No. 1 binds calcium least strongly (i.e. has the highest calcium dependency).

REFERENCES CITED IN THE SPECIFICATION

Suzuki et al., the Journal of Biological Chemistry, Vol. 264, No. 32, Issue of November 15, pp. 18933–18938 (1989).
Hudson et al., Practical Immunology, Third edition (1989), Blackwell Scientific Publications.
Lipman and Pearson (1985) Science 227, 1435.
Sambrook et al., Molecular Cloning: A Laboratory Manual, 2nd Ed., Cold Spring Harbor, 1989.
S. L. Beaucage and M. H. Caruthers, Tetrahedron Letters 22, 1981, pp. 1859–1869.
Matthes et al., The EMBO J. 3, 1984, pp. 801–805.
R. K. Saiki et al., Science 239, 1988, pp. 487–491.
Morinaga et al., 1984, Biotechnology 2, pp. 646–639.
Nelson and Long, Analytical Biochemistry 180, 1989, pp. 147–151.
Hunkapiller et al., 1984, Nature 310, pp. 105–111.
R. Higuchi, B. Krummel, and R. K. Saiki (1988). A general method of in vitro preparation and specific mutagenesis of DNA fragments: study of protein and DNA interactions. Nucl. Acids Res. 16, pp. 7351–7367.
Dubnau et al., 1971, J. Mol. Biol. 56, pp. 209–221.
Gryczan et al., 1978, J. Bacteriol. 134, pp. 318–329.
S. D. Erlich, 1977, Proc. Natl. Acad. Sci. 74, pp. 1680–1682.
Boel et al., 1990, Biochemistry 29, pp. 6244–6249.
Deng and Nickoloff, 1992, Anal. Biochem. 200, pp. 81–88.

We claim:

1. A variant of a parent alpha-amylase enzyme having an increased thermostability or a decreased isoelectric point as compared to the parent enzyme, wherein said parent alpha-amylase has an amino acid sequence having at least an 80% homology to SEQ ID No. 1, SEQ ID No. 2, SEO ID No. 3, and SEQ ID No. 7 and wherein said variant comprises an amino acid substitution which is, or which is equivalent to, one of the following substitutions in the amino acid sequence shown in SEQ ID NO. 1: K269R, P260E, R124P, L217I, Y243F, V206I, L, F, L351C, Q391E, K444Q, N457D, N457E, Q86E, Q346E and Q391E.

2. A variant of a parent alpha-amylase enzyme having an increased thermostability or a decreased isoelectric point as compared to the parent enzyme, wherein said parent alpha-amylase has an amino acid sequence having at least an 80% homology to SEQ ID No. 1, SEQ ID No. 2, SEQ ID No. 3, and SEQ ID No. 7 and wherein said variant comprises a deletion of an amino acid which is, or which is equivalent to T183 or G184 of the amino acid sequence shown in SEQ ID No. 1.

3. A variant of a parent alpha-amylase enzyme having an increased thermostability or a decreased isoelectric point as compared to the parent enzyme, wherein said parent alpha-amylase has an amino acid sequence having at least an 80% homology to SEQ ID No. 1, SEQ ID No. 2, SEQ ID No. 3, and SEQ ID No. 7 and wherein said variant comprises an amino acid substitution which is or which is equivalent to M430C.

4. A variant of a parent alpha-amylase enzyme having an increased stability towards oxidation as compared to the parent enzyme, wherein said parent alpha-amylase has an amino acid sequence having at least an 80% homology to SEQ ID No. 1, SEQ ID No. 2, SEQ ID No. 3, and SEQ ID No. 7 and wherein said variant comprises a substitution of said parent at M202 and deletion at positions 183 and 184 of the amino acid shown in SEQ ID NO. 2.

5. A variant of a parent alpha-amylase enzyme, said parent having at least a 90% homology to the amino acid sequence depicted in SEQ ID No. 1, SEQ ID No. 2, and SEQ ID No. 7 wherein said variant comprises one of the following mutations selected from the group consisting of:

L351C+M430C+del(T183-G184);

Y243P+del (183-184);

Q391E+K444Q, del (183-184)+R124P; and del (183-184)+L351C+M430C+Y243F+Q391E+K444Q.

* * * * *